(12) United States Patent
Sayre et al.

(10) Patent No.: US 9,528,119 B2
(45) Date of Patent: Dec. 27, 2016

(54) TRANSGENIC CELLS WITH INCREASED PLASTOQUINONE LEVELS AND METHODS OF USE

(71) Applicant: Los Alamos National Security, LLC, Los Alamos, NM (US)

(72) Inventors: Richard T. Sayre, Los Alamos, NM (US); Sowmya Subramanian, Los Alamos, NM (US); Edgar Cahoon, Lincoln, NE (US)

(73) Assignee: LOS ALAMOS NATIONAL SECURITY, LLC, Los Alamos, NM (US)

( * ) Notice: Subject to any disclaimer, the term of this patent is extended or adjusted under 35 U.S.C. 154(b) by 211 days.

(21) Appl. No.: 14/307,180

(22) Filed: Jun. 17, 2014

(65) Prior Publication Data
US 2014/0370603 A1    Dec. 18, 2014

Related U.S. Application Data

(60) Provisional application No. 61/836,045, filed on Jun. 17, 2013.

(51) Int. Cl.
*C12N 15/82*    (2006.01)

(52) U.S. Cl.
CPC ....... *C12N 15/8261* (2013.01); *C12N 15/8269* (2013.01)

(58) Field of Classification Search
CPC ................................................ C12N 15/8269
USPC ....................................................... 800/298
See application file for complete search history.

(56) References Cited

U.S. PATENT DOCUMENTS

| 2008/0086787 A1* | 4/2008 | Valentin | .................. | C07K 14/47 800/286 |
|---|---|---|---|---|
| 2014/0041076 A1* | 2/2014 | Stacey | ............... | C12N 15/8247 800/260 |

OTHER PUBLICATIONS

Sadre, R. et al. FEBS Letters (2006) vol. 580; pp. 5357-5362.*
Rippert, P. et al. (2004) Plant Physiology, vol. 134; pp. 92-100.*
*Chlamydomonas reinhardtii* Pathway: plastoquinone biosynthesis, http://http://chlamypw.mpimp-golm.mpg.de/CHLAMY/new-image?object=PWY-1581&type=PATHWAY, accessed Jun. 5, 2013 (2 pages).
Falk et al., "Constitutive overexpression of barley 4-hydroxyphenylpyruvate dioxygenase in tobacco results in elevation of the vitamin E content in seeds but not in leaves," *FEBS Letters* vol. 540, pp. 35-40, 2003.
Perrine et al., "Optimization of Photosynthetic Light Energy Utilization by Microalgae," *Algal Research* vol. 1, pp. 134-142, 2012.
Subramanian et al., "Enhancing photosynthetic energy conversion efficiency through increased plastoquinone pool size," $3^{rd}$ *International Conference on Algal Biomass, Biofuels and Bioproducts*, Jun. 17, 2014 (1 page).
Tian et al., "The *pds2* mutation is a lesion in the *Arabidopsis* homogentisate solanesyltransferase gene involved in plastoquinone biosynthesis," *Planta* vol. 226, pp. 1067-1073, 2007.

* cited by examiner

*Primary Examiner* — Russell Kallis
(74) *Attorney, Agent, or Firm* — Klarquist Sparkman, LLP

(57) ABSTRACT

Disclosed herein are transgenic cells expressing a heterologous nucleic acid encoding a prephenate dehydrogenase (PDH) protein, a heterologous nucleic acid encoding a homogentisate solanesyl transferase (HST) protein, a heterologous nucleic acid encoding a deoxyxylulose phosphate synthase (DXS) protein, or a combination of two or more thereof. In particular examples, the disclosed transgenic cells have increased plastoquinone levels. Also disclosed are methods of increasing cell growth rates or production of biomass by cultivating transgenic cells expressing a heterologous nucleic acid encoding a PDH protein, a heterologous nucleic acid encoding an HST protein, a heterologous nucleic acid encoding a DXS protein, or a combination of two or more thereof under conditions sufficient to produce cell growth or biomass.

22 Claims, 10 Drawing Sheets

House-keeping gene rbcL

PDH : 1773 bp
HST : 2130 bp
psbA: 1110 bp
rbcL : 427 bp

PDH

HST

SEQUENCE LISTING

```
<160> NUMBER OF SEQ ID NOS: 10

<210> SEQ ID NO 1
<211> LENGTH: 1359
<212> TYPE: DNA
<213> ORGANISM: Saccharomyces cerevisiae

<400> SEQUENCE: 1
atggtatcag aggataagat tgagcaatgg aaagccacaa aagtcattgg tataattggt      60
ctgggtgata tgggcctatt atacgctaat aaatttacag atgctggatg gggtgttata     120
tgttgtgata gggaagaata ttatgatgaa ctgaaagaaa aatatgcctc agctaaattc     180
gaactggtga aaaatggtca tttggtatcc aggcaaagcg actatattat ctatagtgtt     240
gaagcatcca atattagtaa gatcgtcgca acgtatggac catcttctaa ggttggaaca     300
attgttgggg gtcaaacgag ttgtaagctg ccggaaatcg aggctttcga aaagtattta     360
cccaaggact gcgacatcat taccgtgcat tcccttcatg ggcctaaagt taatactgaa     420
ggccaaccac tagttattat caatcacaga tcacagtacc cagaatcttt tgagttcgtt     480
aattctgtta tggcatgttt gaaaagtaag caagtttatt tgacatatga agagcatgac     540
aagattaccg ctgatacaca agctgtgaca catgctgctt tcttaagtat gggatctgcg     600
tgggcaaaga taaagattta tccttggact ctgggtgtaa acaaatggta cggtggccta     660
```

-continued

```
gaaaatgtga aagttaatat atcactaaga atctattcga acaagtggca tgtttacgca      720
ggattagcca taacaaaccc aagtgcacat cagcaaattc ttcaatatgc aaccagtgca      780
acagaactat ttagtttaat gatagataac aaagaacaag aacttactga tagactatta      840
aaagctaagc aatttgtatt tggaaagcat actggtctct tactattgga tgacacgatt      900
ttagagaaat attcgctatc aaaaagcagc attggtaaca gcaacaattg caagccagtg      960
ccgaattcac atttatcatt gttggcgatt gttgattcgt ggtttcaact tggtattgat     1020
ccatatgatc atatgatttg ttcgacgcca ttattcagaa tattcctggg tgtgtccgaa     1080 tatcttttt taaaacctgg cttattagaa cagacaattg atgcagctat ccatgataaa     1140
tcattcataa aagatgattt agaatttgtt atttcggcta gagaatggag ctcggttgtt     1200
tcttttgcca attttgatat atacaaaaag caatttcaga gtgttcaaaa gttctttgag     1260
ccaatgcttc cagaggctaa tctcattggc aacgagatga taaaaaccat tctgagtcat     1320
tctagtgacc gttcggccgc tgaaaaaaga aatacataa                            1359
```

<210> SEQ ID NO 2
<211> LENGTH: 452
<212> TYPE: PRT
<213> ORGANISM: Saccharomyces cerevisiae

<400> SEQUENCE: 2

```
Met Val Ser Glu Asp Lys Ile Glu Gln Trp Lys Ala Thr Lys Val Ile
1               5                   10                  15

Gly Ile Ile Gly Leu Gly Asp Met Gly Leu Leu Tyr Ala Asn Lys Phe
            20                  25                  30

Thr Asp Ala Gly Trp Gly Val Ile Cys Cys Asp Arg Glu Glu Tyr Tyr
        35                  40                  45

Asp Glu Leu Lys Glu Lys Tyr Ala Ser Ala Lys Phe Glu Leu Val Lys
    50                  55                  60

Asn Gly His Leu Val Ser Arg Gln Ser Asp Tyr Ile Ile Tyr Ser Val
65                  70                  75                  80

Glu Ala Ser Asn Ile Ser Lys Ile Val Ala Thr Tyr Gly Pro Ser Ser
                85                  90                  95

Lys Val Gly Thr Ile Val Gly Gly Gln Thr Ser Cys Lys Leu Pro Glu
            100                 105                 110

Ile Glu Ala Phe Glu Lys Tyr Leu Pro Lys Asp Cys Asp Ile Ile Thr
        115                 120                 125

Val His Ser Leu His Gly Pro Lys Val Asn Thr Glu Gly Gln Pro Leu
    130                 135                 140

Val Ile Ile Asn His Arg Ser Gln Tyr Pro Glu Ser Phe Glu Phe Val
145                 150                 155                 160

Asn Ser Val Met Ala Cys Leu Lys Ser Lys Gln Val Tyr Leu Thr Tyr
                165                 170                 175

Glu Glu His Asp Lys Ile Thr Ala Asp Thr Gln Ala Val Thr His Ala
            180                 185                 190

Ala Phe Leu Ser Met Gly Ser Ala Trp Ala Lys Ile Lys Ile Tyr Pro
        195                 200                 205

Trp Thr Leu Gly Val Asn Lys Trp Tyr Gly Leu Glu Asn Val Lys
        210                 215                 220

Val Asn Ile Ser Leu Arg Ile Tyr Ser Asn Lys Trp His Val Tyr Ala
225                 230                 235                 240

Gly Leu Ala Ile Thr Asn Pro Ser Ala His Gln Gln Ile Leu Gln Tyr
```

```
            245                 250                 255
Ala Thr Ser Ala Thr Glu Leu Phe Ser Leu Met Ile Asp Asn Lys Glu
        260                 265                 270

Gln Glu Leu Thr Asp Arg Leu Leu Lys Ala Lys Gln Phe Val Phe Gly
            275                 280                 285

Lys His Thr Gly Leu Leu Leu Leu Asp Asp Thr Ile Leu Glu Lys Tyr
        290                 295                 300

Ser Leu Ser Lys Ser Ser Ile Gly Asn Ser Asn Asn Cys Lys Pro Val
305                 310                 315                 320

Pro Asn Ser His Leu Ser Leu Leu Ala Ile Val Asp Ser Trp Phe Gln
                325                 330                 335

Leu Gly Ile Asp Pro Tyr Asp His Met Ile Cys Ser Thr Pro Leu Phe
            340                 345                 350

Arg Ile Phe Leu Gly Val Ser Glu Tyr Leu Phe Leu Lys Pro Gly Leu
        355                 360                 365

Leu Glu Gln Thr Ile Asp Ala Ala Ile His Asp Lys Ser Phe Ile Lys
    370                 375                 380

Asp Asp Leu Glu Phe Val Ile Ser Ala Arg Glu Trp Ser Ser Val Val
385                 390                 395                 400

Ser Phe Ala Asn Phe Asp Ile Tyr Lys Lys Gln Phe Gln Ser Val Gln
                405                 410                 415

Lys Phe Glu Pro Met Leu Pro Glu Ala Asn Leu Ile Gly Asn Glu
            420                 425                 430

Met Ile Lys Thr Ile Leu Ser His Ser Ser Asp Arg Ser Ala Ala Glu
        435                 440                 445

Lys Arg Asn Thr
    450

<210> SEQ ID NO 3
<211> LENGTH: 1075
<212> TYPE: DNA
<213> ORGANISM: Arabidopsis thaliana

<400> SEQUENCE: 3
atgtgttctc aggttggtgc tgctgagtct gatgatccag tgctggatag aattgcccgg      60
ttccaaaatg cttgctggag atttcttaga ccccatacaa tccgcggaac agctttagga     120
tccactgcct tggtgacaag agctttgata gagaacactc atttgatcaa atggagtctt     180
gtactaaagg cactttcagg tcttcttgct cttatttgtg ggaatggtta tatagtcggc     240
atcaatcaga tctacgacat tggaatcgac aaagtgaaca aaccatactt gccaatagca     300
gcaggagatc tatcagtgca gtctgcttgg ttgttagtga tattttttgc gatagcaggg     360
cttttagttg tcggatttaa ctttggtcca ttcattacaa gcctatactc tcttggcctt     420
tttctgggaa ccatctattc tgttccaccc ctcagaatga aagattccc agttgcagca      480 tttcttatta ttgccacggt acgaggtttc cttcttaact tggtgtgta ccatgctaca      540 agagctgctc ttggacttcc atttcagtgg agtgcacctg tggcgttcat cacatctttt     600
gtgacactgt ttgcactggt cattgctatt acaaaggacc ttcctgatgt tgaaggagat     660
cgaaagttcc aaatatcaac cctggcaaca aaacttggag tgagaaacat tgcattcctc     720
ggttctggac ttctgctagt aaattatgtt tcagccatat cactagcttt ctacatgcct     780
caggttttta gaggtagctt gatgattcct gcacatgtga tcttggcttc aggcttaatt     840
ttccagacat gggtactaga aaaagcaaac tacaccaagg aagctatctc aggatattat     900
```

```
cggtttatat ggaatctctt ctacgcagag tatctgttat tccccttcct ctagctttca    960
atttcatggt gaggatatgc agttttcttt gtatatcatt cttcttcttc tttgtagctt   1020
ggagtcaaaa tcggttcctt catgtacata catcaaggat atgtccttct gagca        1075
```

<210> SEQ ID NO 4
<211> LENGTH: 317
<212> TYPE: PRT
<213> ORGANISM: Arabidopsis thaliana

<400> SEQUENCE: 4

```
Met Cys Ser Gln Val Gly Ala Ala Glu Ser Asp Asp Pro Val Leu Asp
1               5                   10                  15

Arg Ile Ala Arg Phe Gln Asn Ala Cys Trp Arg Phe Leu Arg Pro His
            20                  25                  30

Thr Ile Arg Gly Thr Ala Leu Gly Ser Thr Ala Leu Val Thr Arg Ala
        35                  40                  45

Leu Ile Glu Asn Thr His Leu Ile Lys Trp Ser Leu Val Leu Lys Ala
    50                  55                  60

Leu Ser Gly Leu Leu Ala Leu Ile Cys Gly Asn Gly Tyr Ile Val Gly
65                  70                  75                  80

Ile Asn Gln Ile Tyr Asp Ile Gly Ile Asp Lys Val Asn Lys Pro Tyr
                85                  90                  95

Leu Pro Ile Ala Ala Gly Asp Leu Ser Val Gln Ser Ala Trp Leu Leu
            100                 105                 110

Val Ile Phe Phe Ala Ile Ala Gly Leu Leu Val Val Gly Phe Asn Phe
        115                 120                 125

Gly Pro Phe Ile Thr Ser Leu Tyr Ser Leu Gly Leu Phe Leu Gly Thr
    130                 135                 140

Ile Tyr Ser Val Pro Pro Leu Arg Met Lys Arg Phe Pro Val Ala Ala
145                 150                 155                 160

Phe Leu Ile Ile Ala Thr Val Arg Gly Phe Leu Leu Asn Phe Gly Val
                165                 170                 175

Tyr His Ala Thr Arg Ala Ala Leu Gly Leu Pro Phe Gln Trp Ser Ala
            180                 185                 190

Pro Val Ala Phe Ile Thr Ser Phe Val Thr Leu Phe Ala Leu Val Ile
        195                 200                 205

Ala Ile Thr Lys Asp Leu Pro Asp Val Glu Gly Asp Arg Lys Phe Gln
    210                 215                 220

Ile Ser Thr Leu Ala Thr Lys Leu Gly Val Arg Asn Ile Ala Phe Leu
225                 230                 235                 240

Gly Ser Gly Leu Leu Leu Val Asn Tyr Val Ser Ala Ile Ser Leu Ala
                245                 250                 255

Phe Tyr Met Pro Gln Val Phe Arg Gly Ser Leu Met Ile Pro Ala His
            260                 265                 270

Val Ile Leu Ala Ser Gly Leu Ile Phe Gln Thr Trp Val Leu Glu Lys
        275                 280                 285

Ala Asn Tyr Thr Lys Glu Ala Ile Ser Gly Tyr Tyr Arg Phe Ile Trp
    290                 295                 300

Asn Leu Phe Tyr Ala Glu Tyr Leu Leu Phe Pro Phe Leu
305                 310                 315
```

```
<210> SEQ ID NO 5
<211> LENGTH: 20
<212> TYPE: DNA
<213> ORGANISM: Artificial Sequence
<220> FEATURE:
<223> OTHER INFORMATION: PDH/HST forward amplification primer

<400> SEQUENCE: 5
ctaggcagtg gcgcgatgac                                              20

<210> SEQ ID NO 6
<211> LENGTH: 24
<212> TYPE: DNA
<213> ORGANISM: Artificial Sequence
<220> FEATURE:
<223> OTHER INFORMATION: PDH/HST reverse amplification primer

<400> SEQUENCE: 6
ggccgctcta gctagaacta gtgg                                         24

<210> SEQ ID NO 7
<211> LENGTH: 23
<212> TYPE: DNA
<213> ORGANISM: Artificial Sequence
<220> FEATURE:
<223> OTHER INFORMATION: psbA forward primer

<400> SEQUENCE: 7
atgacagcaa ttttagaacg tcg                                          23

<210> SEQ ID NO 8
<211> LENGTH: 29
<212> TYPE: DNA
<213> ORGANISM: Artificial Sequence
<220> FEATURE:
<223> OTHER INFORMATION: psbA reverse primer

<400> SEQUENCE: 8
tagaacgtcg tgaaaattct agcctatgg                                    29

<210> SEQ ID NO 9
<211> LENGTH: 23
<212> TYPE: DNA
<213> ORGANISM: Artificial Sequence
<220> FEATURE:
<223> OTHER INFORMATION: PDH RT-PCR forward primer

<400> SEQUENCE: 9
ccgctgaaaa aagaaataca taa                                          23

<210> SEQ ID NO 10
<211> LENGTH: 21
<212> TYPE: DNA
<213> ORGANISM: Artificial Sequence
<220> FEATURE:
<223> OTHER INFORMATION: PDH RT-PCR reverse primer

<400> SEQUENCE: 10
cttttttcag cggccgaacg g                                            21
```

TRANSGENIC CELLS WITH INCREASED PLASTOQUINONE LEVELS AND METHODS OF USE

CROSS REFERENCE TO RELATED APPLICATIONS

This claims the benefit of U.S. Provisional Application No. 61/836,045, filed Jun. 17, 2013, which is incorporated herein by reference in its entirety.

ACKNOWLEDGMENT OF GOVERNMENT SUPPORT

This invention was made with government support under Contract No. DEAC52-06NA25396 awarded by the U.S. Department of Energy. The government has certain rights in the invention.

FIELD

This disclosure relates to transgenic cells and methods of use, particularly transgenic cells having increased levels of plastoquinone.

BACKGROUND

Environmentally sustainable energy production and reduction of greenhouse gas emissions can be achieved by use of carbon-neutral energy sources. Wind, geothermal, solar, hydroelectric, and biofuels are now being developed as sustainable sources of domestic energy production. Unlike wind, solar, or hydroelectric energy sources, biofuels can be converted into energy-dense, liquid fuels that are compatible with current energy distribution and consumption systems. Since biofuels have the potential to reduce global carbon emission, they are an attractive part of the mix of sustainable energy solutions. In addition, oil-based biofuels are one of the few renewable, energy-dense fuels that can be used by the aviation and shipping transportation sectors. However, demands for food and environmental sustainability limit the use of crops or plants for biofuel production.

Unicellular algae are a prime candidate for production of biofuels. In contrast to plants, unicellular algae do not partition large amounts of biomass into supportive structures such as stems and roots. Under near ideal growth conditions algae direct most of their energy into cell division (6-12 hour cycle), allowing for rapid biomass accumulation. Under stress conditions (e.g., low nitrogen) or in the presence of exogenous reductants (sugar, glycerol) metabolism is redirected towards the production of energy-dense storage compounds such as lipids. Many unicellular algae are facultatively capable of producing 4% to 60% lipids per gram dry weight under the appropriate growth conditions (e.g., stress or photoheterotrophic growth), making them one of the most efficient biofuel production systems known. It has been estimated that, on area basis, algae may produce up to twenty times the fuel of any land plant system. Despite these useful characteristics, many challenges remain for developing efficient, large-scale production of biofuel from algae.

SUMMARY

Disclosed herein are transgenic photosynthetic cells (for example plant or algae cells) and methods of making and using such cells. In some examples, the transgenic cells express a heterologous nucleic acid encoding a prephenate dehydrogenase (PDH) protein, a heterologous nucleic acid encoding a homogentisate solanesyl transferase (HST) protein, a heterologous nucleic acid encoding a deoxyxylulose phosphate synthase (DXS) protein, or a combination of two or more thereof. In some examples, the transgenic cells express a heterologous nucleic acid encoding a PDH protein and a heterologous nucleic acid encoding a HST protein. In some embodiments, the transgenic photosynthetic cells are plant cells (such as canola or *Camelina* cells). In other embodiments, the transgenic photosynthetic cells are algae cells (such as *Chlamydomonas* cells).

The disclosed transgenic cells are useful for a variety of applications, including production of biofuels. In particular examples, the disclosed transgenic cells have increased plastoquinone (PQ) levels compared to a control, for example compared to cells lacking the transgene(s) described herein. Increasing the amount of PQ in a photosynthetic cell increases photosynthetic efficiency (for example by reducing non-photochemical quenching (NPQ) by the xanthophylls cycle but increase NPQ through direct quenching of chlorophyll excited states, and/or increasing photochemical quenching), increases cell growth rates, and/or increases production of biomass. Therefore, disclosed herein are methods of increasing PQ levels in photosynthetic cells (such as plant or algae cells) by expressing a heterologous nucleic acid encoding a PDH protein, a heterologous nucleic acid encoding an HST protein, a heterologous nucleic acid encoding a DXS protein, or a combination of two or more thereof (such as a heterologous nucleic acid encoding a PDH protein and a heterologous nucleic acid encoding an HST protein).

The disclosed methods also include methods of increasing cellular growth rates or production of biomass compared to a control (for example compared to cells lacking the transgene(s) described herein) by cultivating a transgenic cell expressing a heterologous nucleic acid encoding a PDH protein, a heterologous nucleic acid encoding an HST protein, a heterologous nucleic acid encoding a DXS protein, or a combination of two or more thereof (such as a heterologous nucleic acid encoding a PDH protein and a heterologous nucleic acid encoding an HST protein) under conditions sufficient to produce cell growth or biomass.

The foregoing and other features of the disclosure will become more apparent from the following detailed description, which proceeds with reference to the accompanying figures.

SEQUENCE LISTING

Figure 1:
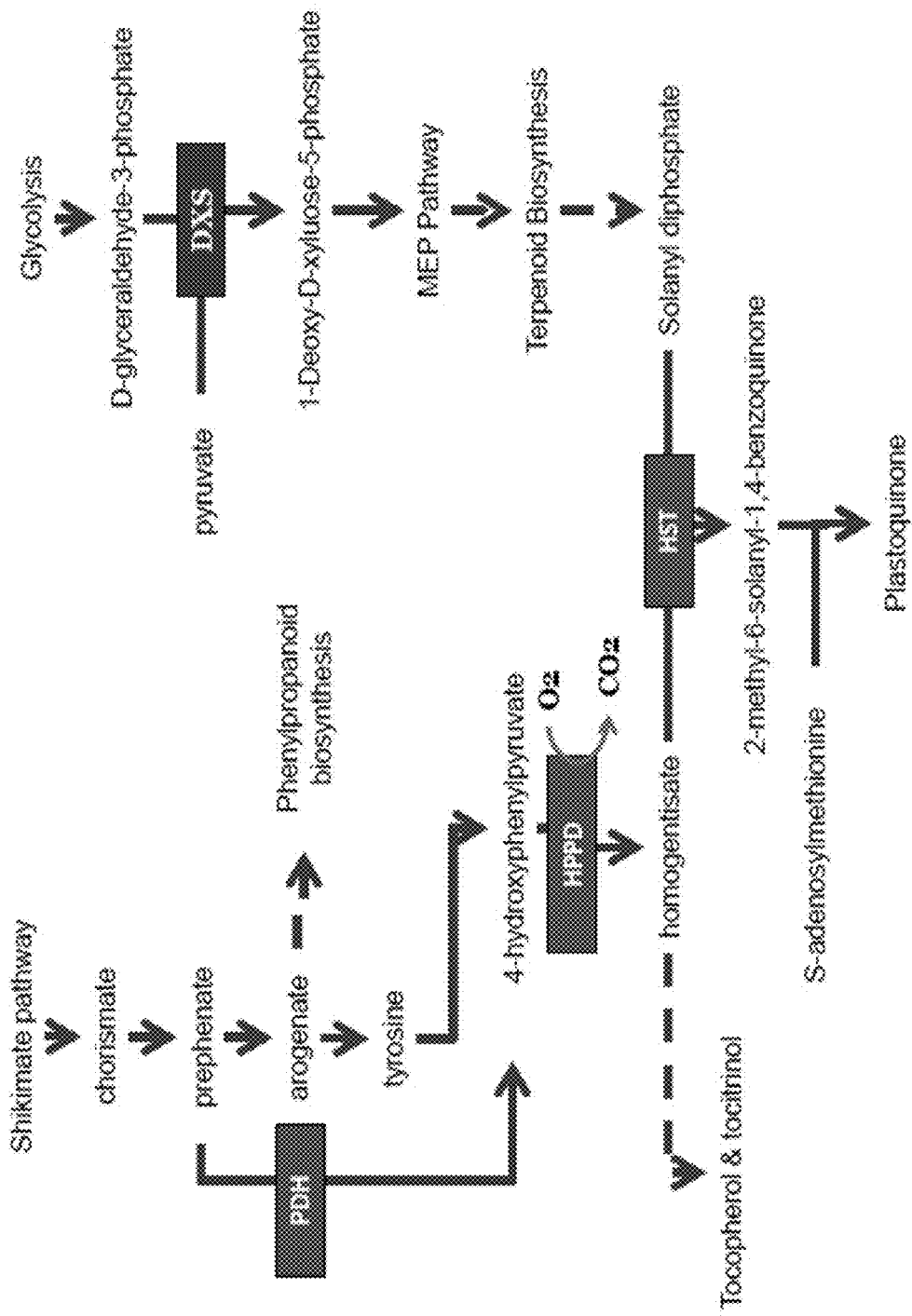
FIG. 1 is a schematic diagram showing a portion of the biosynthetic pathway for plastoquinone in algae. PDH, prephenate dehydrogenase; HPPD, 4-hydroxyphenyl pyruvate dioxygenase; HST, homogentisate solanesyl transferase; DXS, deoxyxylulose phosphate synthase.

Any nucleic acid and amino acid sequences listed herein or in the accompanying sequence listing are shown using standard letter abbreviations for nucleotide bases and amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jun. 16, 2014, and is 11,577 bytes, which is incorporated by reference herein.

SEQ ID NOs: 1 and 2 are an exemplary codon optimized PDH nucleic acid sequence and a PDH amino acid sequence, respectively.

SEQ ID NOs: 3 and 4 are exemplary HST nucleic acid and amino acid sequences, respectively.

SEQ ID NOs: 5 and 6 are nucleic acid sequences of forward and reverse primers, respectively, for amplification of PDH or HST in transgenic algae.

SEQ ID NOs: 7 and 8 are nucleic acid sequences of forward and reverse psbA primers, respectively.

SEQ ID NOs: 9 and 10 are nucleic acid sequences of forward and reverse PDH primers, respectively

DETAILED DESCRIPTION

The slowest step (1 ms) in photosynthetic electron transfer is the oxidation of dihydroplastoquinone (plastoquinol; $PQH_2$) by the cytochrome b6f (Cytb6f) complex. PQ plays a critical role in buffering the fast rate (1 µs) of photosystem II (PSII) electron transfer and the slow rate (1 ms) of $PQH_2$ oxidation by the $Cytb_6f$ complex. The PQ pool size in thylakoid membranes is small, about 8 PQ/PSII/Cytb6f complex (Kruk and Karpinski, *Biochim. Biophys. Acta* 1757:1669-1675, 2006). PQ also has a limited half-life in the membrane of about 9 hours (Wanke et al., *Plant Sci.* 154:183-187, 2000). It is shown herein that by increasing the thylakoid PQ pool size (e.g., in algae cells), the electron and proton buffering capacity of the thylakoid membrane and threshold light intensity at which non-photochemical quenching is activated are increased. Without being bound by theory, it is believed that increased PQ pool size enhances energy conversion efficiency by indirectly reducing the optical cross section of the light harvesting antennae complex by quenching excess chlorophyll excited states at high light intensities, reducing generation of reactive oxygen species which damage the photosynthetic machinery. In addition, the larger PQ pool size buffers transient fluxes in electron transfer rates in non-equilibrium situations, such as fluctuating light intensities.

The rate of $PQH_2$ oxidation by the Cytb6f complex is controlled in part by the rate of $PQH_2$ diffusion between PSII and the Cytb6f complex. It has been estimated by percolation theory that the rate of $PQH_2$ diffusion in thylakoid membranes is 1000 times slower than in liposomes due the presence of dispersed macromolecular protein complexes (Kirchhoff et al., *Biochemistry* 41:4872-4882, 2002). By creating thylakoid membrane micro-domains with elevated $PQH_2$ concentrations or by channeling $PQH_2$ transfer, the rate of $PQH_2$ reduction and oxidation is enhanced.

The synthetic pathway for PQ in algae is shown in FIG. 1. The pathway converts prephenate to arogenate, then tyrosine, and ultimately 4-hydroxyphenylpyruvate. The pathway then branches for production of tocopherols or PQ. For production of PQ, 4-hydroxyphenylpyruvate is converted to homogentisate by 4-hydroxyphenylpyruvate dioxygenase. Homogentisate is converted to 2-demethylplastoquinol-9 by HST and then by reduction and oxidation to plastoquinol-9 (PQ). In some embodiments disclosed herein, the conversion of prephenate to 4-hydroxyphenylpyruvate, which normally involves several steps in algae, is achieved in a single step by expression in the algae of a heterologous PDH, for example from yeast. This drives the pathway to the tocopherol/PQ branchpoint, increasing PQ production. In addition, the expression of PDH in chloroplasts may alter the synthesis of aromatic amino acids and their pool sizes. Increasing expression of HST in the algae (for example, by expressing a heterologous HST nucleic acid or overexpressing native algae HST) either separately or simultaneously with PDH expression can also increase PQ production by driving the tocopherol/PQ branchpoint toward the PQ pathway. PQ production in the algae can also be increased by increasing expression of DXS, which is involved in synthesis of isopentenyl diphosphate, the precursor for isoprenoids, including plastoquinone.

I. Abbreviations
Chl chlorophyll
Cytb6f cytochrome b6f complex
DXS deoxyxylulose phosphate synthase
HS high salt medium
HST homogentisate solanesyl transferase
NPQ non-photochemical quenching
PDH prephenate dehydrogenase
$PQH_2$ dihydroplastoquinone (plastoquinol)
PQ plastoquinone
PSII photosystem II II. Terms
Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. All sequence database accession numbers (such as GenBank, EMBL, or UniProt) mentioned herein are incorporated by reference in their entirety as present in the respective database on Jun. 17, 2013. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Algae: A group of autotrophic organisms which range from unicellular to multicellular forms. Unicellular algae are commonly referred to as microalgae. Microalgae include *Achnanthes, Amphora, Borodinella, Botryococcus, Chaetoceros, Chlorococcum, Chlorella, Chlamydomonas, Cyclotella, Dunaliella, Galdieria, Pleurochrysis, Monoraphidium, Nannochloris, Nannochloropsis, Navicula, Nitzschia, Oocysitis, Oscillatoria, Phaeodactylum, Scenedesmus, Stichococcus, Synechococcus, Tetraselmis,* and *Thalassiosira*. Macroalgae (seaweed) include *Gracilaria* and *Sargassum*.

Biomass: Biological material from living or recently living organisms. In some examples, biomass is the mass of living biological organisms in a given area, volume, or ecosystem at a given time. Biomass is the amount of cellular material in a cultivation system (such as a bioreactor, pond, or other container) at a point in time. The amount of biomass can be determined by the number of cells present, wet weight, dry weight, amount of a cellular constituent (such as chlorophyll-a), absorbance (e.g., $OD_{750}$), or any other measurement known to one of ordinary skill in the art.

Conservative variants: A substitution of an amino acid residue for another amino acid residue having similar biochemical properties. "Conservative" amino acid substitutions are those substitutions that do not substantially affect or decrease an activity of a polypeptide (such as PDH polypeptide, an HST polypeptide, or a DXS polypeptide). A polypeptide can include one or more amino acid substitutions, for example 1-10 conservative substitutions, 2-5 conservative substitutions, 4-9 conservative substitutions, such as 1, 2, 5 or 10 conservative substitutions. Specific, non-limiting examples of a conservative substitution include the following examples (Table 1).

TABLE 1

Exemplary conservative amino acid substitutions

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

The term conservative variation also includes the use of a substituted amino acid in place of an unsubstituted parent amino acid, provided that the substituted polypeptide retains an activity of the unsubstituted polypeptide.

Control: A sample or standard used for comparison with an experimental sample. In some examples, the control is a cell (or a culture of cells) that does not contain one or more transgenes which are included in the cell (or culture) for comparison. For example, a cell that does not contain a heterologous PDH nucleic acid can be a control for a cell that contains a heterologous PDH nucleic acid. In some examples, the control cell is a wild type (or non-transgenic) cell. In other examples, the control cell is a transgenic cell, but one that does not contain at least one transgene of interest. For example, a cell that contains a heterologous PDH nucleic acid can be a control for a cell that contains a heterologous HST nucleic acid, but does not contain a heterologous PDH nucleic acid. In still other examples, a control cell may be a wild type complement cell, such as a deletion mutant (such as a psbA deletion mutant) that is transformed with a nucleic acid encoding the deleted nucleic acid, but not any additional nucleic acid, such as a heterologous PDH, HST, DXS, or other nucleic acid.

Cultivation or Culturing: Intentional growth of an organism or cell, such as an alga (for example, *Chlamydomonas*) or plant cell in the presence of assimilable sources of carbon, nitrogen, and mineral salts. In an example, such growth can take place in a solid or semi-solid nutritive medium, or in a liquid medium in which the nutrients are dissolved or suspended. In a further example, the cultivation may take place on a surface or by submerged culture. The nutritive medium can be composed of complex nutrients or can be chemically defined.

Deoxyxylulose phosphate synthase (DXS): An enzyme that catalyzes the thiamin diphosphate-dependent condensation of pyruvate and D-glyceraldehyde-3-phosphate to yield 1-deoxy-D-xylulose 5-phosphate. 1-deoxy-D-xylulose 5-phosphate is converted to isopentenyl diphosphate, which is the precursor for isoprenoids, including plastoquinone. DXS nucleic acid and amino acid sequences are publicly available. One of ordinary skill in the art can identify DXS nucleic acid and amino acid sequences. Exemplary, non-limiting, DXS sequences are provided herein.

Expression: Transcription or translation of a nucleic acid sequence. For example, a gene is expressed when its DNA is transcribed into an RNA or RNA fragment, which in some examples is processed to become mRNA. A gene may also be expressed when its RNA or mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Gene: A segment of nucleic acid that encodes an individual protein or RNA molecule (also referred to as a "coding sequence" or "coding region") and may include non-coding regions ("introns") and/or associated regulatory regions such as promoters, operators, terminators and the like, that may be located upstream or downstream of the coding sequence.

Heterologous: Originating from a different genetic source or species or present at a genetic locus other than the naturally occurring genetic locus in the organism. In some examples, a gene or nucleic acid that is heterologous to a cell originates from an organism or species other than the cell in which it is expressed (for example from a different species). In other examples, a gene or nucleic acid that is heterologous to a cell is present at a different genetic locus (such as on a different chromosome, at a different location in a chromosome, or exogenous to a chromosome, such as on a plasmid) than the naturally occurring genetic locus in the cell. In further examples, a heterologous nucleic acid may include a duplication of a naturally occurring nucleic acid, such that two (or more) copies of the nucleic acid are present in the cell or organism, for example at the genetic locus of the naturally occurring copy of the nucleic acid. Methods for introducing a heterologous gene or nucleic acid in a cell or organism are well known in the art, for example transformation with a nucleic acid, including electroporation, lipofection, and particle gun acceleration.

Homogentisate solanesyl transferase (HST): Also known as homogentisate prenyltransferase. An enzyme capable of catalyzing the condensation of homogentisate and solanesyl diphosphate to form 2-demethylplastoquinol-9 (e.g., Tian et al., *Planta* 226:1067-1073, 2007). In subsequent steps in the PQ biosynthetic pathway, 2-demethylplastoquinol-9 is methylated and oxidized to form PQ. HST nucleic acid and amino acid sequences are publicly available and can be identified by one of ordinary skill in the art. Exemplary, non-limiting, HST sequences are provided herein.

Isolated: An "isolated" biological component (such as a nucleic acid molecule, protein, or cell) has been substantially separated or purified away from other biological components, such as components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In some examples, a promoter sequence is operably linked to a protein-encoding sequence, such that the promoter drives transcription of the linked nucleic acid and/or expression of the protein.

Photosynthetic cell: A cell that is able to convert light energy (for example, solar energy) to chemical energy. Photosynthetic cells contain light sensitive pigments, such as chlorophyll, that capture solar energy. Chlorophyll and other light sensitive pigments are typically present in cells in chloroplast organelles. Exemplary photosynthetic cells are plant cells and algae cells (including macroalgae and microalgae cells).

Plant cell: Any cell derived from a plant, including cells from undifferentiated tissue (e.g., callus) as well as plant seeds, pollen, propagules and embryos. Plant cells can be obtained from any plant organ or tissue and cultures prepared therefrom.

Plastoquinone (PQ): A quinone molecule involved in the electron transport chain of photosynthesis. Plastoquinone is reduced (accepts two protons ($H^+$) from the stromal matrix of the chloroplast, coupled to two electrons ($e^-$) from photosystem II), forming plastoquinol. It transports the protons to the lumen of thylakoid discs, while the electrons continue through the electron transport chain into the cytochrome b6f protein complex. Plastoquinones have from six to nine isoprenoid units. Plastoquinone-9 has the structure:

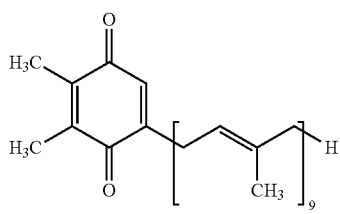

Prephenate dehydrogenase (PDH): Also known as Tyr1. An enzyme capable of catalyzing the transformation of prephenate to 4-hydroxyphenylpyruvate. 4-hydroxyphenylpyruvate is converted to homogentisate, by hydroxyphenyl dioxygenase. Homogentisate is the branchpoint for synthesis of tocopherols and PQ. PDH nucleic acid and amino acid sequences are publicly available and can be identified by one of ordinary skill in the art. Exemplary, non-limiting, PDH sequences are provided herein.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Promoters may be constitutively active, such as a promoter that is continuously active and is not subject to regulation by external signals or molecules. In some examples, a constitutive promoter is active such that expression of a sequence operably linked to the promoter is expressed ubiquitously (for example, in all cells of a tissue or in all cells of an organism and/or at all times in a single cell or organism, without regard to temporal or developmental stage).

Promoters may be inducible or repressible, such that expression of a sequence operably linked to the promoter can be expressed under selected conditions. In some examples, a promoter is an inducible promoter, such that expression of a sequence operably linked to the promoter is activated or increased. An inducible promoter may be activated by presence or absence of a particular molecule, for example, tetracycline, metal ions, alcohol, or steroid compounds. An inducible promoter also includes a promoter that is activated by environmental conditions, for example, light or temperature. In further examples, the promoter is a repressible promoter such that expression of a sequence operably linked to the promoter can be reduced to low or undetectable levels, or eliminated. A repressible promoter may be repressed by direct binding of a repressor molecule (such as binding of the trp repressor to the trp operator in the presence of tryptophan). In a particular example, a repressible promoter is a tetracycline repressible promoter. In other examples, a repressible promoter is a promoter that is repressible by environmental conditions, such as hypoxia or exposure to metal ions.

Purified: The term purified does not require absolute purity; rather, it is intended as a relative term. Thus, for example, a purified preparation of a compound or a cell is one in which the specified compound or cell is more enriched than it is in its generative environment, for instance in a prokaryotic cell or in a cell culture (for example, in cell culture medium). Preferably, a preparation of a specified compound is purified such that the compound represents at least 50% of the total content of the preparation. In some embodiments, a purified preparation contains at least 60%, at least 70%, at least 80%, at least 85%, at least 90%, at least 95% or more of the specified compound.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons. ALIGN compares entire sequences against one another, while LFASTA compares regions of local similarity. These alignment tools and their respective tutorials are available on the Internet. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of a specific protein using ALIGN set to default parameters. Proteins with even greater similarity to a reference sequence will show increasing percentage identities when assessed by this method, such as at least 80%, at least 85%, at least 90%, at least 92%, at least 95%, at least 98%, or at least 99% sequence identity.

When significantly less than the entire sequence is being compared for sequence identity, homologous sequences will typically possess at least 80% sequence identity over short windows of 10-20, and may possess sequence identities of at least 85%, at least 90%, at least 95%, 96%, 97%, 98%, or at least 99%, depending on their similarity to the reference sequence. Sequence identity over such short windows can be determined using LFASTA. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Vector: A nucleic acid molecule as introduced into a host cell (such as an alga or plant cell), thereby producing a transformed host cell. A vector may include nucleic acid sequences that permit it to replicate in a host cell, such as an origin of replication. A vector may also include one or more selectable marker genes and/or other genetic elements known in the art. Vectors include plasmid vectors, including plasmids for expression in plant or algae cells.

III. Transgenic Photosynthetic Cells

Disclosed herein are transgenic photosynthetic cells (for example, plant or algae cells). In various embodiments, the transgenic cells express a heterologous nucleic acid encoding a PDH protein, a heterologous nucleic acid encoding an HST protein, a heterologous nucleic acid encoding a DXS protein, or a combination of two or more thereof. In some embodiments, the transgenic cells express a heterologous nucleic acid encoding a PDH protein. In other embodiments, the transgenic cells express a heterologous nucleic acid encoding an HST protein. In additional embodiments, the transgenic cells express a heterologous nucleic acid encoding a DXS protein. In still further embodiments, the transgenic cells express a heterologous nucleic acid encoding a PDH protein and a heterologous nucleic acid encoding an HST protein. In additional embodiments, the transgenic cells express a heterologous nucleic acid encoding a PDH protein and a heterologous nucleic acid encoding a DXS protein, the transgenic algae express a heterologous nucleic acid encoding an HST protein and a heterologous nucleic acid encoding a DXS protein, or the transgenic algae express a heterologous nucleic acid encoding a PDH protein, a heterologous nucleic acid encoding an HST protein, and a heterologous nucleic acid encoding a DXS protein.

In some embodiments, the transgenic cells have increased PQ amounts, for example as compared to control cell (such as a wild type (non-transgenic) cell of the same strain or species as the transgenic cell, or a transgenic cell that does not express the heterologous PDH, HST, and/or DXS protein). In some examples, the transgenic cells disclosed herein have at least about 5% increased PQ levels (such as at least about 10%, 20%, 30%, 40%, 50%, 60%, 70%, 80%, 90%, 100%, 150%, 200%, 300%, 400%, 500%, or more) as compared to control cells. For example the transgenic cells may have about 5-500% more PQ (such as about 10-400%, 20-300%, 50-250%, 75-200%, 50-150%, 10-100%, 10-75%, or 10-50% more) than a control cell. Methods of determining the amount (quantitatively or relative to a control) of PQ in cells (such as a plant or alga cell or a population of plant or algae cells) are known to one of ordinary skill in the art. These methods include direct measurements (for example, high pressure liquid chromatography or mass spectrometry) or indirect measurements (such as chlorophyll fluorescence or NPQ). In particular examples, the methods described in Example 2, below are used to determine an amount of PQ (such as an increase or decrease in PQ compared to a control) in cells.

In some embodiments, transgenic cells with varying levels of PQ are generated to optimize improvements in photosynthetic energy conversion while maintaining synthesis of other necessary metabolites, such as tocopherols and aromatic amino acids. In some examples, transgenic cells with varying levels of PQ are produced by transforming cells with one or more of the heterologous nucleic acids described herein and screening the resulting cell lines for PQ levels (directly or indirectly). In other examples, transgenic cells with varying levels of PQ are produced by transforming cells with one or more of the heterologous nucleic acids disclosed herein under the control of promoters of varying strength (for example, strong, medium, or weak promoters). Exemplary promoters for use in the transgenic cell lines are discussed below. The resulting cell lines are screened for PQ levels (directly or indirectly), and cell lines with the desired properties are selected. In some non-limiting embodiments, the selected cell lines have an increase of about 1-5-fold in PQ levels as compared to a control cell line.

In additional examples, the properties of the transgenic cells with respect to PQ levels can be evaluated by oxygen evolution measurements. These studies are carried out on thylakoids, with varying time intervals between flashes of light to induce charge separation and oxygen evolution. Without being bound by theory, it is believed that transgenic lines with an increased (e.g., a larger) PQ pool size will be able to restore the oxygen evolution capacity at shorter time intervals compared to ones with a smaller PQ pool size (e.g., a control cell, or a transgenic cell with a smaller increase in the PQ pool size).

In other examples, the relative sensitivity of the transgenic cells to photoinhibition, oxygen evolved is measured while exposing the thylakoids to high light intensities (for example, about 1000 µmoles for 0-30 minutes). It is believed that transgenic cells with a larger PQ pool size will produce more oxygen/[Chl] compared to those with a smaller PQ pool size (e.g., a control cell, or a transgenic cell with a smaller increase in the PQ pool size), and thereby be less sensitive to photoinhibition (e.g., Ruffle et al., *Plant Physiology* 127:633-644, 2001).

A. Prephenate Dehydrogenase (PDH)

Specific transgenic cells disclosed herein express a heterologous pdh nucleic acid. The pdh nucleic acid (such as all or a portion of a pdh gene) encodes a protein capable of catalyzing the transformation of prephenate to 4-hydroxyphenylpyruvate. In non-limiting examples, the pdh nucleic acid or protein is a *Saccharomyces cerevisiae* pdh gene or protein. Nucleic acid and amino acid sequences for pdh are publicly available. For example, GenBank Accession Nos. NM_001178514, Z36035, DQ332878, and FN393060 (nucleotide 542696-544054 (reverse complement)) disclose exemplary yeast pdh nucleic acid sequences. GenBank Accession Nos. NP_009725, CAA85127, and CBK39241 disclose exemplary yeast PDH amino acid sequences. In other examples, the PDH nucleic acid or protein is from yeast (such as *Saccharomyces, Schizosaccharomyces, Candida*, or *Kluveromyces*), a plant (such as *Arabidopsis thaliana, Glycine max, Oryza sativa*, or *Zea mays*), or bacterium (such as *E. coli*). Exemplary pdh nucleic acid sequences include GenBank Accession Nos. NM_001023517 (Schizosaccharomyces), XM_717584 (Candida), XM_455066 (*Kluveromyces*), NM_101439 (*Arabidopsis thaliana*), XM_003545166 or XR_417861 (*Glycine max*), NM_001065074 (*Oryza sativa*), and NM_001153997 (*Zea mays*), each of which is incorporated herein by reference. One of ordinary skill in the art can identify additional PDH nucleic acid and amino acid sequences, for example, PDH sequences from other organisms.

In one non-limiting example, a pdh nucleic is from *S. cerevisiae*. In some examples, the pdh nucleic acid includes or consists of the nucleic acid sequence set forth as:

(SEQ ID NO: 1)
ATGGTATCAGAGGATAAGATTGAGCAATGGAAAGCCACAAAAGTCATTGG

TATAATTGGTCTGGGTGATATGGGCCTATTATACGCTAATAAATTTACAG

ATGCTGGATGGGGTGTTATATGTTGTGATAGGGAAGAATATTATGATGAA

CTGAAAGAAAAATATGCCTCAGCTAAATTCGAACTGGTGAAAAATGGTCA

TTTGGTATCCAGGCAAAGCGACTATATTATCTATAGTGTTGAAGCATCCA

ATATTAGTAAGATCGTCGCAACGTATGGACCATCTTCTAAGGTTGGAACA

ATTGTTGGGGGTCAAACGAGTTGTAAGCTGCCGGAAATCGAGGCTTTCGA

AAAGTATTTACCCAAGGACTGCGACATCATTACCGTGCATTCCCTTCATG

GGCCTAAAGTTAATACTGAAGGCCAACCACTAGTTATTATCAATCACAGA

TCACAGTACCCAGAATCTTTTGAGTTCGTTAATTCTGTTATGGCATGTTT

GAAAAGTAAGCAAGTTTATTTGACATATGAAGAGCATGACAAGATTACCG

CTGATACACAAGCTGTGACACATGCTGCTTTCTTAAGTATGGGATCTGCG

TGGGCAAAGATAAAGATTTATCCTTGGACTCTGGGTGTAAACAAATGGTA

CGGTGGCCTAGAAAATGTGAAAGTTAATATATCACTAAGAATCTATTCGA

ACAAGTGGCATGTTTACGCAGGATTAGCCATAACAAACCCAAGTGCACAT

CAGCAAATTCTTCAATATGCAACCAGTGCAACAGAACTATTTAGTTTAAT

GATAGATAACAAAGAACAAGAACTTACTGATAGACTATTAAAAGCTAAGC

AATTTGTATTTGGAAAGCATACTGGTCTCTTACTATTGGATGACACGATT

TTAGAGAAATATTCGCTATCAAAAAGCAGCATTGGTAACAGCAACAATTG

CAAGCCAGTGCCGAATTCACATTTATCATTGTTGGCGATTGTTGATTCGT

GGTTTCAACTTGGTATTGATCCATATGATCATATGATTTGTTCGACGCCA

TTATTCAGAATATTCCTGGGTGTGTCCGAATATCTTTTTTTAAAACCTGG

CTTATTAGAACAGACAATTGATGCAGCTATCCATGATAAATCATTCATAA

AAGATGATTTAGAATTTGTTATTTCGGCTAGAGAATGGAGCTCGGTTGTT

TCTTTTGCCAATTTTGATATATACAAAAAGCAATTTCAGAGTGTTCAAAA

GTTCTTTGAGCCAATGCTTCCAGAGGCTAATCTCATTGGCAACGAGATGA

TAAAAACCATTCTGAGTCATTCTAGTGACCGTTCGGCCGCTGAAAAAGA

AATACATAA

In some embodiments, a pdh gene of use in the methods disclosed herein has a nucleic acid sequence at least 70%, 75%, 85%, 90%, 95%, 96%, 97%, 98% or 99% identical to the nucleic acid sequence set forth in SEQ ID NO: 1 or any of the PDH GenBank Accession Nos. disclosed herein. Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein. In some examples, the pdh nucleic acid is codon-optimized for expression in the selected organism (such as algae, for example, *Chlamydomonas*).

In some examples, the pdh nucleic acid encodes a protein that includes or consists of the amino acid sequence set forth as:

(SEQ ID NO: 2)
MVSEDKIEQWKATKVIGIIGLGDMGLLYANKFTDAGWGVICCDREEYYDE

LKEKYASAKFELVKNGHLVSRQSDYIIYSVEASNISKIVATYGPSSKVGT

IVGGQTSCKLPEIEAFEKYLPKDCDIITVHSLHGPKVNTEGQPLVIINHR

SQYPESFEFVNSVMACLKSKQVYLTYEEHDKITADTQAVTHAAFLSMGSA

WAKIKIYPWTLGVNKWYGGLENVKVNISLRIYSNKWHVYAGLAITNPSAH

QQILQYATSATELFSLMIDNKEQELTDRLLKAKQFVFGKHTGLLLLDDTI

LEKYSLSKSSIGNSNNCKPVPNSHLSLLAIVDSWFQLGIDPYDHMICSTP

LFRIFLGVSEYLFLKPGLLEQTIDAAIHDKSFIKDDLEFVISAREWSSVV

SFANFDIYKKQFQSVQKFFEPMLPEANLIGNEMIKTILSHSSDRSAAEKR

NT

In some embodiments, the polypeptide encoded by the pdh gene has an amino acid sequence at least 80%, 85%, 90%, 95%, 96%, 97%, 98% or 99% identical to the amino acid sequence set forth in SEQ ID NO: 2 or a polypeptide encoded by any of the PDH GenBank Accession Nos. disclosed herein.

Exemplary nucleic acid and amino acid sequences can be obtained using computer programs that are readily available on the internet and the amino acid sequences set forth herein. In one example, the PDH polypeptide retains a function of the PDH protein, such as catalyzing conversion of prephenate to 4-hydroxyphenylpyruvate. Thus, a specific, non-limiting example of a PDH polypeptide is a conservative variant of the PDH polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided above (Table 1).

B. Homogentisate Solanesyl Transferase (HST)

Specific disclosed transgenic cells express a heterologous hst nucleic acid. The hst nucleic acid (such as all or a portion of an hst gene) encodes a protein capable of catalyzing condensation of homogentisate and solanesyl diphosphate to form 2-demthylplastoquinol-9. In some examples, the hst nucleic acid or protein is an *Arabidopsis thaliana* hst nucleic acid or protein. Nucleic acid and amino acid sequences for hst are publicly available. For example, GenBank Accession Nos. NM_001084669 and NM_001161137 disclose exemplary *A. thaliana* hst nucleic acid sequences. GenBank Accession Nos. NP_001154609 and NP_001078138 disclose exemplary *A. thaliana* HST amino acid sequences. In other examples, the HST nucleic acid or protein is from a plant, such as *Arabidopsis*, corn, rice, or spinach, or an algae, such as *Chlamydomonas* (see e.g., Sadre et al., *J. Biol. Chem.* 285:18191-18198, 2010). Exemplary hst nucleic acid sequences include GenBank Accession Nos.

NM_001066618 (*Oryza sativa*), NM_001153231 (*Zea mays*), and XM_001695289 (*Chlamydomonas reinhardtii*), each of which is incorporated herein by reference. One of ordinary skill in the art can identify additional HST nucleic acid and amino acid sequences, for example, HST sequences from other organisms.

In one non-limiting example, an hst nucleic acid is from *A. thaliana*. In some examples, the hst nucleic acid includes or consists of the nucleic acid sequence set forth as:

(SEQ ID NO: 3)
ATGTGTTCTCAGGTTGGTGCTGCTGAGTCTGATGATCCAGTGCTGGATAG

AATTGCCCGGTTCCAAAATGCTTGCTGGAGATTTCTTAGACCCCATACAA

TCCGCGGAACAGCTTTAGGATCCACTGCCTTGGTGACAAGAGCTTTGATA

GAGAACACTCATTTGATCAAATGGAGTCTTGTACTAAAGGCACTTTCAGG

TCTTCTTGCTCTTATTTGTGGGAATGGTTATATAGTCGGCATCAATCAGA

TCTACGACATTGGAATCGACAAAGTGAACAAACCATACTTGCCAATAGCA

GCAGGAGATCTATCAGTGCAGTCTGCTTGGTTGTTAGTGATATTTTTGC

GATAGCAGGGCTTTTAGTTGTCGGATTTAACTTTGGTCCATTCATTACAA

GCCTATACTCTCTTGGCCTTTTTCTGGGAACCATCTATTCTGTTCCACCC

CTCAGAATGAAAAGATTCCCAGTTGCAGCATTTCTTATTATTGCCACGGT

ACGAGGTTTCCTTCTTAACTTTGGTGTGTACCATGCTACAAGAGCTGCTC

TTGGACTTCCATTTCAGTGGAGTGCACCTGTGGCGTTCATCACATCTTTT

GTGACACTGTTTGCACTGGTCATTGCTATTACAAAGGACCTTCCTGATGT

TGAAGGAGATCGAAAGTTCCAAATATCAACCCTGGCAACAAAACTTGGAG

TGAGAAACATTGCATTCCTCGGTTCTGGACTTCTGCTAGTAAATTATGTT

TCAGCCATATCACTAGCTTTCTACATGCCTCAGGTTTTTAGAGGTAGCTT

GATGATTCCTGCACATGTGATCTTGGCTTCAGGCTTAATTTTCCAGACAT

GGGTACTAGAAAAAGCAAACTACACCAAGGAAGCTATCTCAGGATATTAT

CGGTTTATATGGAATCTCTTCTACGCAGAGTATCTGTTATTCCCCTTCCT

CTAGCTTTCAATTTCATGGTGAGGATATGCAGTTTTCTTTGTATATCATT

CTTCTTCTTCTTTGTAGCTTGGAGTCAAAATCGGTTCCTTCATGTACATA

CATCAAGGATATGTCCTTCTGAGCA

In some embodiments, an hst nucleic acid of use in the methods disclosed herein has a nucleic acid sequence at least 70%, 75%, 85%, 90%, 95%, 96%, 97%, 98% or 99% identical to the nucleic acid sequence set forth in SEQ ID NO: 3 or any of the HST GenBank Accession Nos. disclosed herein. Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein. In some examples, the hst nucleic acid is codon-optimized for expression in the selected organism, (such as algae, for example, *Chlamydomonas*).

In some examples, the hst nucleic acid encodes a protein that includes or consists of the amino acid sequence set forth as:

(SEQ ID NO: 4)
MCSQVGAAESDDPVLDRIARFQNACWRFLRPHTIRGTALGSTALVTRALI

ENTHLIKWSLVLKALSGLLALICGNGYIVGINQIYDIGIDKVNKPYLPIA

AGDLSVQSAWLLVIFFAIAGLLVVGFNFGPFITSLYSLGLFLGTIYSVPP

LRMKRFPVAAFLIIATVRGFLLNFGVYHATRAALGLPFQWSAPVAFITSF

VTLFALVIAITKDLPDVEGDRKFQISTLATKLGVRNIAFLGSGLLLVNYV

SAISLAFYMPQVFRGSLMIPAHVILASGLIFQTWVLEKANYTKEAISGYY

RFIWNLFYAEYLLFPFL

In some embodiments, the polypeptide encoded by the hst nucleic acid has an amino acid sequence at least 80%, 85%, 90%, 95%, 96%, 97%, 98% or 99% identical to the amino acid sequence set forth in SEQ ID NO: 4 or any of the HST GenBank Accession Nos. disclosed herein.

Exemplary nucleic acid and amino acid sequences can be obtained using computer programs that are readily available on the internet and the amino acid sequences set forth herein. In one example, the HST polypeptide retains a function of the HST protein, such as condensation of homogentisate and solanesyl diphosphate to form 2-demthylplastoquinol-9. Thus, a specific, non-limiting example of an HST polypeptide is a conservative variant of the HST polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In one example, an HST polypeptide is a conservative variant of SEQ ID NO: 4, for example including one or more conservative amino acid substitutions (for example 1-10 conservative substitutions, 2-5 conservative substitutions, 4-9 conservative substitutions, such as 1, 2, 5 or 10 conservative substitutions). A table of conservative substitutions is provided above (Table 1).

C. Deoxyxylulose Phosphate Synthase (DXS)

Specific transgenic cells disclosed herein express a heterologous dxs nucleic acid in an algae cell. The dxs nucleic acid (such as all or a portion of a dxs gene) encodes a protein capable of catalyzing the thiamin diphosphate-dependent condensation of pyruvate and glyceraldehyde-3-phosphate to yield 1-deoxy-xylulose 5-phosphate. Nucleic acid and amino acid sequences for dxs are publicly available. In some examples, the DXS nucleic acid or protein is from a bacteria, such as *E. coli*. For example, GenBank Accession No. NC_000913.2 (437539 . . . 439401, complement) discloses an exemplary *E. coli* dxs nucleic acid sequence. GenBank Accession No. NP_414954 discloses an exemplary *E. coli* DXS amino acid sequence. In other examples, the DXS nucleic acid or protein is from a plant, such as *Arabidopsis*, corn, tomato, pepper, spinach, potato, gingko, or cassaya, or an algae, such as *Chlamydomonas* (see e.g., Cordoba et al., *J. Exp. Bot.* 62:2023-2038, 2011; Sayre et al., *Ann. Rev. Plant Biol.* 62:251-272, 2011). Exemplary dxs nucleic acid sequences include GenBank Accession Nos. NM_117647 (*Arabidopsis thaliana*), NM_001247743 (*Solanum lycopersicum*), NM_001288201 (*Solanum tuberosum*), and XM_001702010 (*Chlamydomonas reinhardtii*) each of which is incorporated herein by reference. One of ordinary skill in the art can identify additional DXS nucleic acid and amino acid sequences, for example, DXS sequences from other organisms.

Exemplary nucleic acid and amino acid sequences can be obtained using computer programs that are readily available on the internet and the amino acid sequences set forth herein. In one example, the DXS polypeptide retains a function of the DXS protein, such as condensation of condensation of pyruvate and glyceraldehyde-3-phosphate to yield 1-deoxyxylulose 5-phosphate. Thus, a specific, non-limiting example of a DXS polypeptide is a conservative variant of the DXS polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided above (Table 1).

D. Production of Transgenic Algae Cells

Methods of transforming and cultivating algae are known in the art (e.g., Stern et al., *The Chlamydomonas Sourcebook: A Comprehensive Guide to Biology and Laboratory Use*, Second Edition, Academic Press, 2008). In an embodiment, a nucleic acid molecule can be inserted into one or more expression vectors, using methods known to those of skill in the art. Vectors include one or more expression cassettes including expression control sequences operably linked to the nucleic acid of interest (such as pdh, hst, dxs, or other nucleic acids). An expression cassette includes nucleic acid elements that permit expression of a gene or other nucleic acid in a host cell. Vectors are discussed in more detail below.

Transformation of an alga cell with recombinant DNA can be carried out by conventional techniques as are well known to those of ordinary skill in the art. Methods of transformation include transformation utilizing *Agrobacterium tumifaciens* transformed with a plasmid including the desired nucleic acid. In other examples, algae cells can be transformed utilizing biolistics (e.g., the "gene gun"), electroporation, glass beads, or carbide whiskers. One of ordinary skill in the art can select an appropriate transformation method and vector, based on the cells to be transformed and other desired characteristics.

In some embodiments, the cells are transformed with two or more heterologous nucleic acids. In some examples, each heterologous nucleic acid is separately introduced to the cell, for example in separate transformation vectors. The cells can be transformed with the separate vectors sequentially or simultaneously. In other examples, the two or more heterologous nucleic acids are introduced to the cell in the same transformation vector under the control of the same promoter (for example, a bi-cistronic construct) or under the control of separate promoters. One of ordinary skill in the art can select appropriate vectors and methods to transform cells with two or more heterologous nucleic acids.

In some examples, the heterologous nucleic acid (such as a heterologous nucleic acid encoding a PDH protein, an HST protein, or a DXS protein) is codon-optimized for the cell in which it is to be expressed. Codon usage bias, the use of synonymous codons at unequal frequencies, is ubiquitous among genetic systems (Ikemura, *J. Mol. Biol.* 146:1-21, 1981; Ikemura, *J. Mol. Biol.* 158:573-97, 1982). The strength and direction of codon usage bias is related to genomic G+C content and the relative abundance of different isoaccepting tRNAs (Akashi, *Curr. Opin. Genet. Dev.* 11:660-666, 2001; Duret, *Curr. Opin. Genet. Dev.* 12:640-9, 2002; Osawa et al., *Microbiol. Rev.* 56:229-264, 1992). Codon usage can affect the efficiency of gene expression. Codon-optimization refers to replacement of a codon in a nucleic acid sequence with a synonymous codon (one that codes for the same amino acid) more frequently used (preferred) in the organism. Each organism has a particular codon usage bias for each amino acid, which can be determined from publicly available codon usage tables (for example see Nakamura et al., *Nucleic Acids Res.* 28:292, 2000 and references cited therein). For example, a codon usage database is available on the World Wide Web at www.kazusa.or.jp/codon. One of ordinary skill in the art can modify a nucleic acid encoding a particular amino acid sequence, such that it encodes the same amino acid sequence, while being optimized for expression in a particular cell type (such as an algae cell).

A wide variety of algae species (such as microalgae and/or macroalgae) can be utilized in the methods described herein. In some examples, the algae species include, but are not limited to *Chlorella* (such as *Chlorella vulgaris*), *Chlamydomonas* (such as *Chlamydomonas reinhardtii*), *Chaetoceros, Spirulina* (such as *Spirulina platensis*), *Dunaliella*, and *Porphyridum*. In particular examples, the algae species include algae useful for production of biofuels or other compounds (such as polyunsaturated acids, pigments, or phytochemicals, for example, for nutritional supplements). In some examples, the algae include *Akistrodesmus, Arthrospira, Botryococcus braunii, Chlorella* (such as *Chlorella* sp. or *Chlorella protothecoides*), *Crypthecodinium* (such as *Crypthecodinium cohnii*), *Cyclotella, Dunaliella tertiolecta, Galdieria* (such as *Galdieria sulphuraria*), *Gracilaria, Hantzschia, Haematococcus* (such as *Haematococcus pluvialis*), *Nannochloris, Nannochloropsis, Neochloris oleoabundans, Nitzschia, Phaeodactylum, Pleurochrysis carterae* (also called CCMP647), *Porphyridium, Sargassum, Scenedesmus* (such as *Scenedesmus obliquus*), *Schiochytrium, Stichococcus, Tetraselmis, Thalassiosira pseudonana, Thraustochytrium roseum*, and *Ulkenia* sp. In one example, the algae species is *Chlamydomonas reinhardtii*.

E. Production of Transgenic Plant Cells

Transformation and regeneration of both monocotyledonous and dicotyledonous plant cells is routine, and the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG)-mediated transformation; transformation using viruses; microinjection of plant cells; micro-projectile bombardment of plant cells; vacuum infiltration; and *Agrobacterium tumefaciens* (AT) mediated transformation.

A number of vectors suitable for stable transformation of plant cells or for the establishment of transgenic plants have been described in, e.g., Pouwels et al. (*Cloning Vectors: A Laboratory Manual*, 1985, Suppl., 1987), Weissbach and Weissbach (*Meth. Plant Mol. Bio.*, Academic Press, 1989) and Gelvin et al. (*Plant Molecular Biology Manual*, Kluwer Academic Publishers, 1990). In addition, one of ordinary skill in the art is aware of the components useful in a transformation vector, and will be able to select and assemble such components in order to tailor make a vector for their specific use. Additional vectors are discussed below.

In some embodiments, the cells are transformed with two or more heterologous nucleic acids. In some examples, each heterologous nucleic acid is separately introduced to the cell, for example in separate transformation vectors. The cells can be transformed with the separate vectors sequentially or simultaneously. In other examples, the two or more heterologous nucleic acids are introduced to the cell in the same transformation vector under the control of the same promoter (for example, a bi-cistronic construct) or under the control of separate promoters. One of ordinary skill in the art can select appropriate vectors and methods to transform cells with two or more heterologous nucleic acids.

Numerous methods for transforming plant cells with recombinant DNA are known in the art and may be used. Two commonly used methods for plant transformation are *Agrobacterium*-mediated transformation and microprojectile bombardment. Microprojectile bombardment methods (e.g., the "gene gun") are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

Transformation methods are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants, e.g. various media and recipient target cells, transformation of immature embryos and subsequent regeneration of fertile transgenic plants are disclosed in U.S. Pat. Nos. 6,194,636 and 6,232,526, which are incorporated herein by reference.

Following transformation and regeneration of plants with the transformation vector, transformed plants may be selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic. After transformed plants are selected and grown to maturity, they can be assayed using the methods described herein, and other methods appropriate to the synthetic construct of the transgene, to determine whether the introduced nucleic acid(s) are being produced.

The seeds of transgenic plants can be harvested from fertile transgenic plants and be used to grow progeny generations of transformed plants including hybrid plant lines for screening of plants having an enhanced agronomic trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced agronomic trait, e.g. enhanced yield, can be crossed with transgenic plant line having other recombinant DNA that confers another trait, e.g. herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA Progeny plants carrying DNA for both parental traits can be crossed back into the female parent line multiple times, e.g. usually 6 to 8 generations, to produce a progeny plant with substantially the same genotype as one original transgenic parental line, but for the recombinant DNA of the other transgenic parental line In the practice of transformation DNA is typically introduced into only a small percentage of target cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (val), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Cells that survive exposure to the selective agent, or cells that have been scored positive in a screening assay, may be cultured in regeneration media and allowed to mature into plants. Developing plantlets can be transferred to plant growth mix, and hardened off, e.g., in an environmentally controlled chamber at about 85% relative humidity, 600 ppm $CO_2$, and 25-250 microeinsteins $m^{-2} s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, e.g. self-pollination is commonly used with transgenic corn. The regenerated transformed plant or its progeny seed or plants can be tested for expression of the recombinant DNA and screened for the presence of enhanced agronomic trait.

In some examples, callus and suspension cultures can be established from the disclosed transgenic plant cells by protocols known in the art. Suspension cultures can be raised from a callus culture and maintained in fresh suspension medium. Suitable nutrient media for plant cell suspension culture are well known to one of skill in the art.

In a particular example, a plant cell suspension medium includes Murashige and Skoog (MS) salts (e.g., Cat. No. M524, Phytotech, Shawnee Mission, Kans.) and Nitsch and Nitsch vitamins (e.g., Cat. No. N608; Phytotech, Shawnee Mission, Kans.). See, e.g., Nitsch and Nitsch, *Science* 163: 85-87, 1969. Suspension cultures can be established by aseptically transferring a known mass of cells expressed as packed cell volume (PCV) to fresh medium on a regular schedule, typically at 7-14 day intervals. Medium for suspension culture ("suspension medium") can be optimized for initiation of suspension culture or for desired characteristics.

Representative, non-limiting example plant cells that can be used in the methods described herein include *Arabidopsis*; field crops (e.g. alfalfa, barley, bean, clover, corn, cotton, flax, false flax (*Camelina*), lentils, maize, oats, pea, rape/canola, rice, rye, safflower, sorghum, soybean, sugarcane, sunflower, tobacco, and wheat); vegetable crops (e.g. asparagus, beet, *brassica* generally, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g. almond, apple, apricot, banana, blackberry, blueberry, cacao, cassaya, cherry, citrus, coconut, cranberry, date, hazelnut, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); tree woods and ornamentals (e.g. alder, ash, aspen, azalea, birch, boxwood, camellia, carnation, chrysanthemum, elm, fir, grasses (such as switch grass or *Miscanthus*), ivy, jasmine, juniper, oak, palm, poplar, pine, redwood, rhododendron, rose, and rubber).

F. Transformation and Expression Constructs

One of ordinary skill in the art can select or construct vectors for transformation and expression of heterologous nucleic acids in cells (such as plant or algae cells). Typically, transformation and expression vectors include, for example, one or more nucleic acids under the transcriptional control of 5' and 3' regulatory sequences and a dominant selectable marker. For example, genes that confer antibiotic resistance or sensitivity to the plasmid may be used as selectable markers. Such expression vectors also can contain a promoter regulatory region (e.g., a regulatory region controlling inducible or constitutive, environmentally-or developmentally-regulated, or cell- or tissue-specific expression), a transcription initiation start site, a ribosome binding site, an RNA processing signal, a transcription termination site, and/or a polyadenylation signal.

In some embodiments, the promoters selected for vectors of use in the disclosed methods are chloroplast promoters. In one example, the nucleic acid is placed under the control of the strong constitutive promoter (for example an alpha subunit of ATP synthase (atpA) promoter). Additional promoters suitable for use in chloroplast gene expression include the 16S RNA promoter, the beta subunit of the ATP synthase (atpB) promoter, the ribulose-1,5-bisphosphate carboxylase/oxygenase large subunit (rbcL) promoter, the photosystem II D1 protein (psbA), promoter, the ribulose bisphosphate carboxylase (RBCS2) promoter, or the HSP70A-RBCS2 tandem promoter.

In some examples, a strong, medium, or weak strength promoter may be selected to tune the amount of transgenic protein produced, and thus produce transgenic cell lines with varying PQ pool levels. Promoter strength can be determined by measuring rates of transcription from a promoter, for example in an in vitro or in vivo system. In certain embodiments, a strong promoter is one which promotes transcription of RNA at high levels, for example at levels such that the transcriptional activity of the promoter generally accounts for about 5% or more of the transcriptional activity of all transcription within a cell. The strength of a promoter is often cell or tissue-specific and thus may vary from one cell type to another. In some examples, the rbcL, psbA, and atpB promoters are strong promoters, while the atpA promoter is a weaker promoter. See e.g., Blowers et al., *Plant Cell* 2:1059-1070, 1990; Hwang et al., *Proc. Natl. Acad. Sci. USA* 93:996-1000, 1996; Salvador et al., *Plant J.* 3:213-219, 1993; Silk and Wu, *Plant Mol. Biol.* 23:87-96, 1993.

In additional embodiments, the nucleic acids disclosed herein are introduced into the nuclear genome (for example, in a vector including a nuclear gene promoter). In such examples, the expression vector also includes a chloroplast targeting sequence operably linked to the 5' end of the nucleic acid to be expressed. Examples of chloroplast targeting sequences (for example, sequences encoding chloroplast "transit peptides") are known to one of ordinary skill in the art, and include those from rbcS, Cab, DnaJ-J8, biotin carboxyl carrier protein (BCCP), protochlorophyllide oxidoreductase A (PORA), ferredoxin-dependent glutamate synthase 2 (GLU2), tocopherol cyclase (TOCC), and most Calvin cycle enzymes (e.g., Rubisco small subunit, phosphoglycerate kinase, and glyceraldehyde 3-phosphate dehydrogenase). See, e.g., Lee et al., *Plant Cell* 20:1603-1622, 2008; Jang et al., *Mol. Breeding.* 9:81-91, 2002; incorporated herein by reference in their entirety.

Examples of additional promoters that can be used in the present disclosure include, but are not limited to the Cauliflower mosaic virus 35S promoter, SV40 promoter, the CMV enhancer-promoter, the CMV enhancer/β-actin promoter, and the tissue-specific promoter probasin. Other promoter sequences that can be used to construct nucleic acids and practice methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

Examples of additional strong promoters include, but are not limited to: viral promoters (such as CaMV 35S or CoYMV), ubiquitin promoter (such as Ubi-1 from maize), actin promoter (e.g, Act from rice), atpA promoter, nopaline synthase promoter, and the octopine synthase promoter, pEMU promoter, MAS promoter, or a H3 histone promoter.

Inducible promoters or gene-switches are used to both spatially and temporally regulate gene expression. By allowing the time and/or location of gene expression to be precisely regulated, gene-switches or inducible promoters may control deleterious and/or abnormal effects caused by overexpression or non-localized gene expression. Thus, for a typical inducible promoter in the absence of the inducer, there would be little or no gene expression while, in the presence of the inducer, expression should be high (e.g., off/on). Examples of stimulus-responsive promoters include, but are not limited to hormone-responsive promoters (e.g., ethanol inducible alcR-encoded transcriptional activator (ALCR), a promoter derived from alcA), light-inducible promoters (such as rbcS promoter, Cab promoter), metal-inducible promoters, heat-shock promoters, wound-inducible and stress-inducible (e.g., drought stress, salt stress, shear stress, nutrient stress) promoters. Others are activated by chemical stimuli, such as IPTG or Tetracycline (Tet), or galactose. Other promoters are responsive to pathogen infection or insect damage.

A number of controllable gene expression systems have been devised, including those regulated by light (e.g., the pea rbcS-3A promoter, Kuhlemeier et al., *The Plant Cell*, 1:471-478, 1989, and the maize rbcS promoter, Schaffner and Sheen, *Plant Cell* 3:997, 1991), heat (Callis et al., *Plant Physiol.* 88:965, 1988; Ainley and Key, *Plant Mol. Biol.*, 14:949-967, 1990; Holtorf et al., *Plant Mol. Biol.* 29:637-646, 1995), pathogens (PR1-a; Williams et al., *Biotechnology* 10:540-543, 1992; Gatz, *Annu. Rev. Plant Physiol. Plant Mol. Biol.* 48:89-108, 1997), herbicide safeners (In2-2, GST-27; De Veylder et al., *Plant Cell Physiol.* 38:568-577, 1997), wounding (Firek et al. *Plant Mol. Biol.* 22:129-212, 1993), ethanol (Salter et al., *Plant J.* 16:127-132, 1998), phytohormones (Li et al., *Plant Cell* 3:1167-1175, 1991), steroids (Aoyama and Chua, *Plant J.*, 11:605-612, 1997), wounding (e.g., wunI, Siebertz et al., *Plant Cell* 1:961, 1989), hormones, such as abscisic acid (Marcotte et al., *Plant Cell* 1:969, 1989); chemicals such as methyl jasminate or salicylic acid (see Gatz et al., *Ann. Rev. Plant Physiol. Plant Mol. Biol.* 48:89-108 1997), and tetracycline (Gatz et al., *Plant J.* 2:397-404, 1992; Weinmann et al., *Plant J.,* 5:559-569, 1994; Sommer et al., *Plant Cell Rep.* 17:891-896, 1998) (from Granger & Cyr, *Plant Cell Reports* 20:227-234, 2001).

In another embodiment, a promoter is a tissue-specific, cell-specific, or developmental stage-specific promoter, which promotes transcription in a single cell or tissue type, a narrow range of cells or tissues, or in one or more specific developmental stages, or at least promotes measurable more transcription in such. Examples of such promoters include, but are not limited to: anther-specific, embryo-specific, endosperm-specific, floral-specific, leaf-specific, meristem-specific, nodule-specific, phloem-specific, seed-specific, stem-specific, stomata-specific, trichome-specific, root-specific, tapetum-specific, and xylem-specific promoters. See, for instance, Carpenter et al., *The Plant Cell* 4:557-571, 1992, Denis et al., *Plant Physiol.* 101:1295-1304 1993, Opperman et al., *Science* 263:221-223, 1993, Stockhause et al., *The Plant Cell* 9:479-489, 1997; Roshal et al., *EMBO J.* 6:1155, 1987; Schernthaner et al., *EMBO J.* 7:1249, 1988; and Bustos et al., *Plant Cell* 1:839, 1989.

It is specifically contemplated that useful promoters will include promoters present in plant or algae genomes as well as promoters from other sources, including nopaline synthase (nos) promoter and octopine synthase (ocs) promoters carried on tumor-inducing plasmids of *Agrobacterium tumefaciens*, caulimovirus promoters such as the cauliflower mosaic virus or figwort mosaic virus promoters. For instance, see U.S. Pat. Nos. 5,322,938 and 5,858,742 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 5,420,034 which discloses a napin promoter, U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806 which discloses a coixin promoter, U.S. 2002/0192813 A1 which discloses 5', 3' and intron elements useful in the design of effective plant expression vectors, U.S. 2004/0216189 A1 which discloses a maize chloroplast aldolase promoter, and U.S. 2004/0123347 A1 which discloses water-deficit inducible promoters, all of which are incorporated herein by reference. These and numerous other promoters that function in plant and algae cells are known to those skilled in the art and available for use in recombinant polynucleotides of the present disclosure to provide for expression of desired nucleic acids in transgenic plant or algae cells.

In one example, a specific transformation and expression vector for algae is a pBA155 plasmid including the desired heterologous nucleic acid(s) (e.g., Minagawa and Crofts, *Photosynth. Res.* 42:121-131, 1994). Additional vectors for transforming algae, such as additional chloroplast transformation vectors are known to one of ordinary skill in the art. These include pD1, pD1-SAA, and pAtpA (Rasala and Mayfield, *Bioengineered Bugs* 2:50-54, 2010), inducible chloroplast expression vectors (e.g., Surzycki et al., *Proc. Natl. Acad. Sci. USA* 104:17548-17553, 2007), and others that can be identified by one of ordinary skill in the art.

IV. Methods of Increasing Plastoquinone Levels in Transgenic Cells

Also disclosed herein are methods of producing a photosynthetic cell (such as a plant or alga cell) with an increased amount of PQ compared to a control cell. In some examples, the methods include expressing in cell a heterologous nucleic acid encoding a PDH protein, a heterologous nucleic acid encoding an HST protein, a heterologous nucleic acid encoding a DXS protein, or a combination of two or more thereof. In some embodiments, the transgenic cells express a heterologous nucleic acid encoding a PDH protein. In other embodiments, the transgenic cells express a heterologous nucleic acid encoding an HST protein. In additional embodiments, the transgenic cells express a heterologous nucleic acid encoding a DXS protein. In still further embodiments, the transgenic cells express a heterologous nucleic acid encoding a PDH protein and a heterologous nucleic acid encoding an HST protein.

In some embodiments, the method produces transgenic cells having at least about 5% higher PQ levels (such as at least about 10%, 20%, 30%, 40%, 50%, 60%, 70%, 80%, 90%, 100%, 150%, 200%, 300%, 400%, 500%, or more) as compared to control cells (such as a wild type (non-transgenic) cell of the same strain or species as the transgenic cell or a transgenic cell that does not express the heterologous PDH, HST, and/or DXS protein). For example the method may produce transgenic cells having about 5-500% more PQ (such as about 10-400%, 20-300%, 50-250%, 75-200%, 50-150%, 10-100%, or 10-50% more) than a control cell. Methods of determining the amount (quantitatively or relative to a control) of PQ in a cell (such as a cell or a population of cells) are known to one of ordinary skill in the art. These methods include direct measurements (for example, high pressure liquid chromatography or mass spectrometry) or indirect measurements (such as chlorophyll fluorescence or NPQ). In some examples, the methods described in Example 2, below are used to determine an amount of PQ (such as an increase or decrease in PQ compared to a control).

V. Methods of Increasing Biomass Production

Disclosed herein are methods of increasing photosynthetic cell biomass production, for example by cultivating one or more of the transgenic cells (such as a transgenic plant or alga cell) disclosed herein. In some embodiments, the transgenic cells express a heterologous nucleic acid encoding a PDH protein. In other embodiments, the transgenic cells express a heterologous nucleic acid encoding an HST protein. In additional embodiments, the transgenic cells express a heterologous nucleic acid encoding a DXS protein. In still further embodiments, the transgenic cells express a heterologous nucleic acid encoding a PDH protein and a heterologous nucleic acid encoding an HST protein.

In some embodiments, cultivating the transgenic cells disclosed herein produces at least about 1.2-fold more biomass (such as at least about 1.3-fold, 1.4-fold, 1.5-fold, 1.75-fold, 2-fold, 2.25-fold, 2.5-fold, 2.75-fold, 3-fold, 3.25-fold, 3.5-fold, 3.75-fold, 4-fold, 4.25-fold, 4.5-fold, 4.75-fold, 5-fold, 5.25-fold, 5.5-fold, 5.75-fold, 6-fold, 7-fold, 8-fold, 9-fold, 10-fold, 15-fold, 20-fold, or more) as compared to control cells cultivated under the same growth conditions (such as wild type (non-transgenic) cells of the same strain or species as the transgenic cells or transgenic cells that do not express the heterologous PDH, HST, and/or DXS protein). For example the transgenic cells may produce about 1.2-50-fold more biomass (such as about 2-20-fold, about 3-10-fold, about 2-10-fold, about 3-6-fold, or about 1-5-fold more biomass) than control cells. The amount of biomass in a culture can be determined by the number of cells present, wet weight, dry weight, amount of a cellular constituent (such as chlorophyll-a), absorbance (e.g., $OD_{750}$), or any other measurement known to one of ordinary skill in the art.

Methods of cultivating plant and algae cells are well known to one of ordinary skill in the art and include those described herein. The transgenic cells of the present disclosure can be cultured in conventional fermentation bioreactors, which include, but are not limited to, batch, fed-batch, cell recycle, and continuous fermenters. The cultivation can also be conducted in shake flasks, test tubes, microtiter dishes, or petri plates. Transgenic cells can also be cultivated in outdoor open ponds or raceways. Cultivation of the cells is carried out at a temperature, pH, oxygen content, and light conditions appropriate for the particular recombinant species. Such culturing conditions are well within the expertise of one of ordinary skill in the art.

Figure 6A:
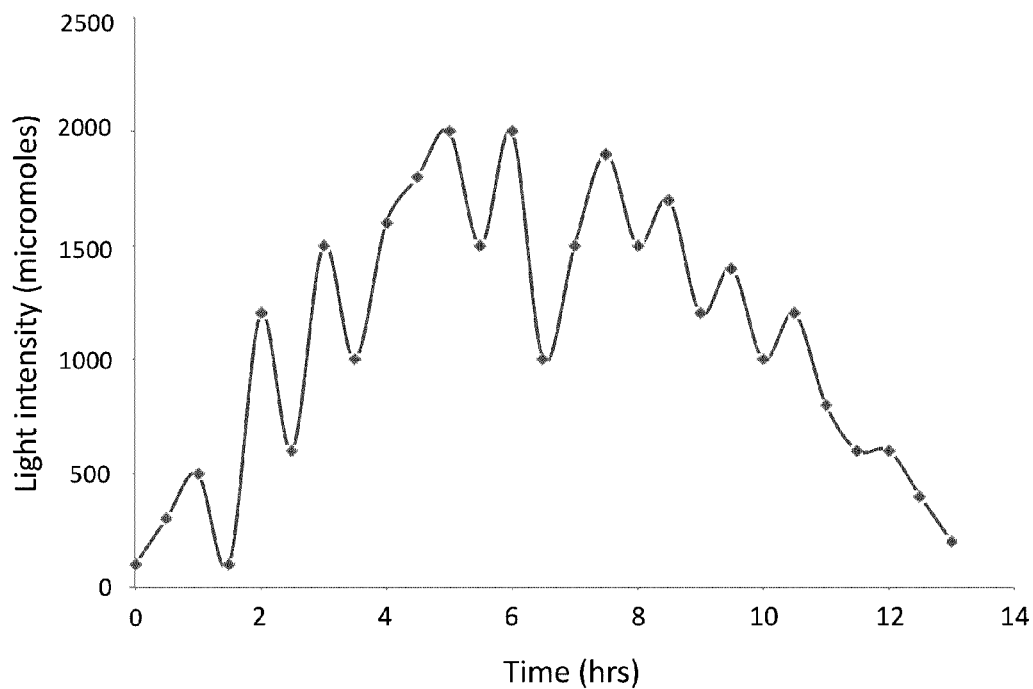
FIGS. 6A and 6B are a pair of graphs showing fluctuating (FIG. 6A) and regular (FIG. 6B) light-dark regimes for algae growth.
Figure 6B:
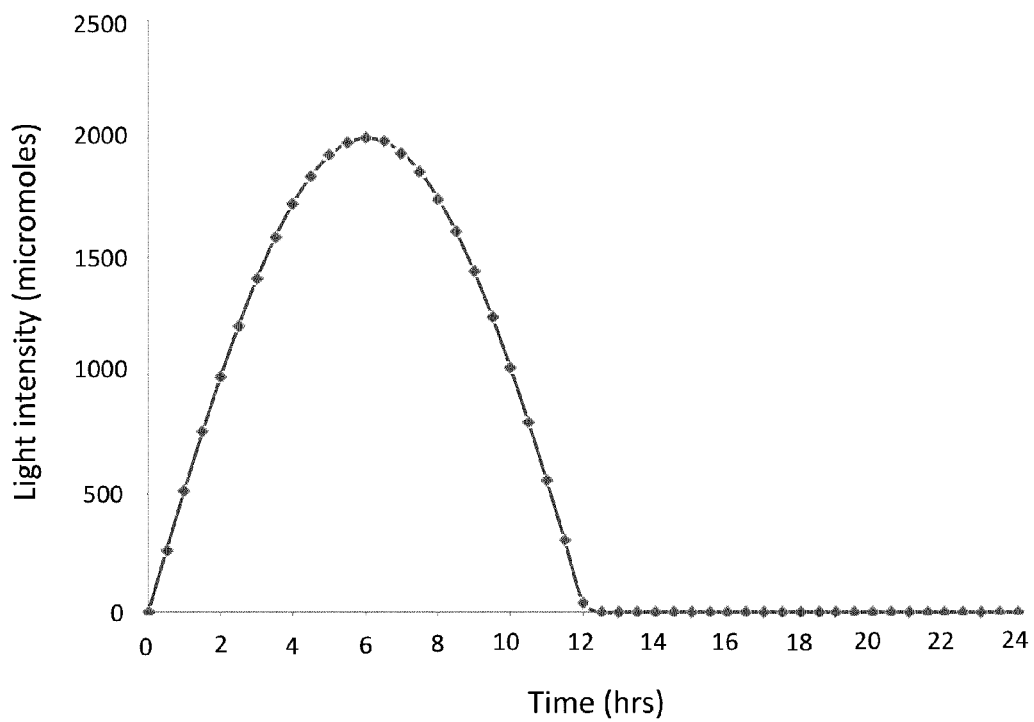

In some examples, the cells are cultivated in a liquid medium. In some examples, the cells are cultured in the liquid medium for about 12 hours or more, for example, about 12, hours, 24 hours, 36 hours, 48 hours, 60 hours, 72 hours, 84 hours, 96 hours, or more. In further examples, the cells are cultured for about 1 day to about 20 days or more, such as about 1, 2, 3, 4, 5, 6, 7, 8, 9, 10, 11, 12, 13, 14, 15, 16, 17, 18, 19, 20 days, or more. In one example, the cells are cultured for at least 24 hours. The cells can be grown with a light-dark cycle, such as periods of alternating light and dark. In some examples, the cells are be grown on a standard light/dark regimen, for example alternating periods of about 8-16 hours of light and about 8-16 hours of dark. In some examples, the light-dark cycle alternates periods of about 16 hours of light with periods of about 8 hours of dark. In other examples, the light-dark cycle alternates periods of about 12 hours of light with periods of about 12 hours of dark. In other examples, the light-dark cycle includes shorter periods of light and dark (for example periods of light and dark from about 0.5 to about 4 hours). Such light-dark cycles are referred to herein as "fluctuating" light cycles. In some examples, the fluctuating light cycles are not constant, for example the periods of light are not all of the same length and/or the periods of dark are not all of the same length. An exemplary fluctuating light-dark cycle is shown in FIG. 6A and an exemplary regular light-dark cycle is shown in FIG. 6B. In both the standard (or "regular") light-dark cycles and the fluctuating light-dark cycles, the light intensity may be gradually increased and/or decreased during the light or dark phase, such that the light-dark designation is not an all-or-none state. In some examples, the light-dark cycle is designed to provide a selected amount of light (μmoles of photons) over the total light-dark cycle. In some examples, the amount of light provided over a period of about 12-13 hours is about 14,000-16,000 μmoles of photons. Photobioreactors which can be programmed for the desired light-dark cycle and light intensity are commercially available (e.g., Phenometrics, Inc., Lansing, Mich.; Photon System Instruments, Drasov, Czech Republic; Qubit Systems, Kingston, Ontario, Canada).

Production of increased biomass is useful for production of products from plants or algae, such as lipids useful for biofuel. Methods of extracting lipid from cells (such as plant or algae cells) are well known to one of ordinary skill in the art. In some examples, the cells are lysed, for example by sonication or mechanical disruption (for example using a French press or glass beads). Suitable methods for lipid extraction include, but are not limited to hexane solvent extraction, Soxhlet extraction, supercritical fluid extraction, extraction/expeller press, and ultrasonic-assisted extraction. See, e.g., Brennan and Owende, *Renewable and Sustainable Energy Reviews* 14:557-577, 2010. Other products that can be obtained from the disclosed transgenic cells include pigments, nutritional supplements (such as omega-3 fatty acids), food sources, high value lipids, carotenoids, food stuffs, and other products.

The following examples are provided to illustrate certain particular features and/or embodiments. These examples should not be construed to limit the disclosure to the particular features or embodiments described.

EXAMPLE 1

Generation of PDH and HST Transgenic Algae

This example describes the production of transgenic algae cell lines expressing heterologous PDH or HST proteins.

Figure 2A:
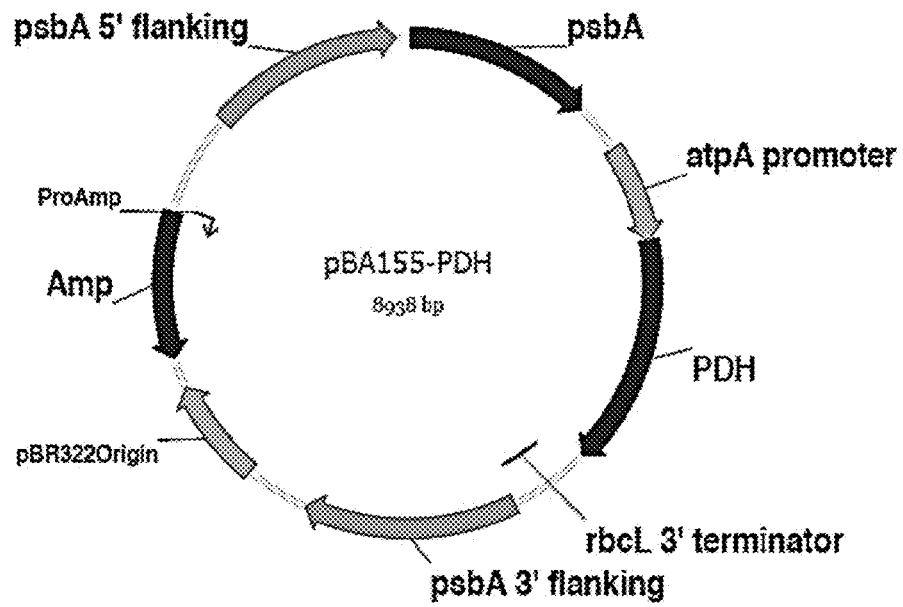
FIGS. 2A and 2B are a pair of diagrams of PDH and HST expression vectors, respectively, used to generate transgenic *Chlamydomonas reinhardtii* cell lines.
Figure 2B:
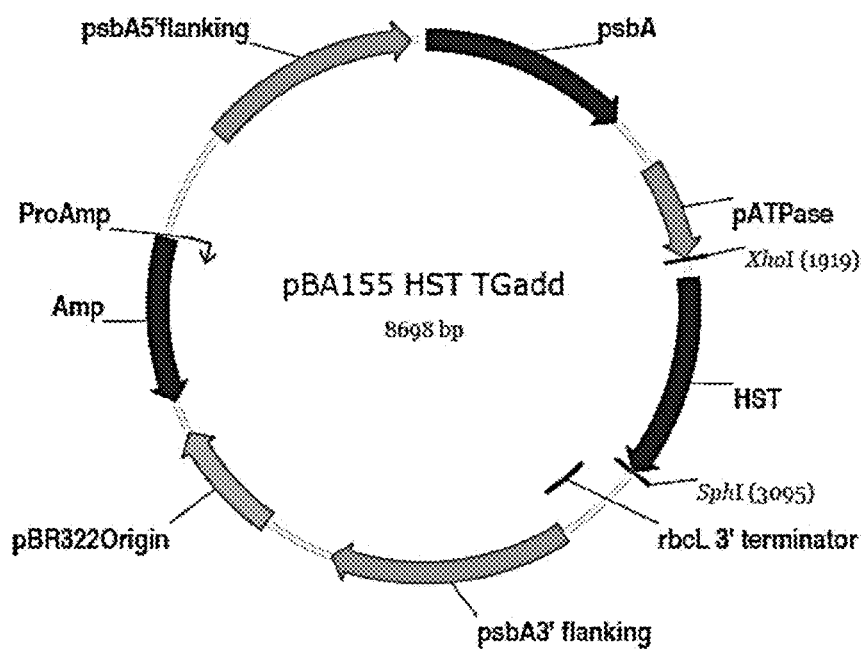

A chloroplast transformation vector was used to express the pdh or hst gene in algae cells. The pBA155 vector, which restores photosynthesis upon successful homologous recombination of the psbA gene (coding for the D1 protein of photosystem II), along with the gene of interest (Minagawa and Crofts, *Photosynth. Res.* 42:121-131, 1994). A codon-optimized yeast PDH encoding nucleic acid (SEQ ID NO: 1) or an *A. thaliana* HST-encoding nucleic acid (SEQ ID NO: 3) was inserted in the pBA155 vector, which expresses the inserted gene under the control of a strong promoter, atpA. FIGS. 2A and B show schematic diagrams of the PDH and HST plasmids, respectively.

The psbA-deficient *Chlamydomonas reinhardtii* strain CC-4147 was grown to log phase in TAP media and coated onto sterile TAP plates. The cells were bombarded with plasmid DNA coated with gold particles. High pressure helium gas carrying the coated gold particles serve as projectiles that bombard the algae cells, delivering the DNA to the cells. Successful transformation results from homologous recombination of the plasmid DNA to the chloroplast genomic DNA, restoring the psbA gene activity (and therefore restoration photosynthesis). Wild type-complement cells (WT-c) are cells in which the deletion mutant lacking the chloroplast encoded psbA gene is complemented with the transforming plasmid containing just the psbA gene.

Figure 3A:
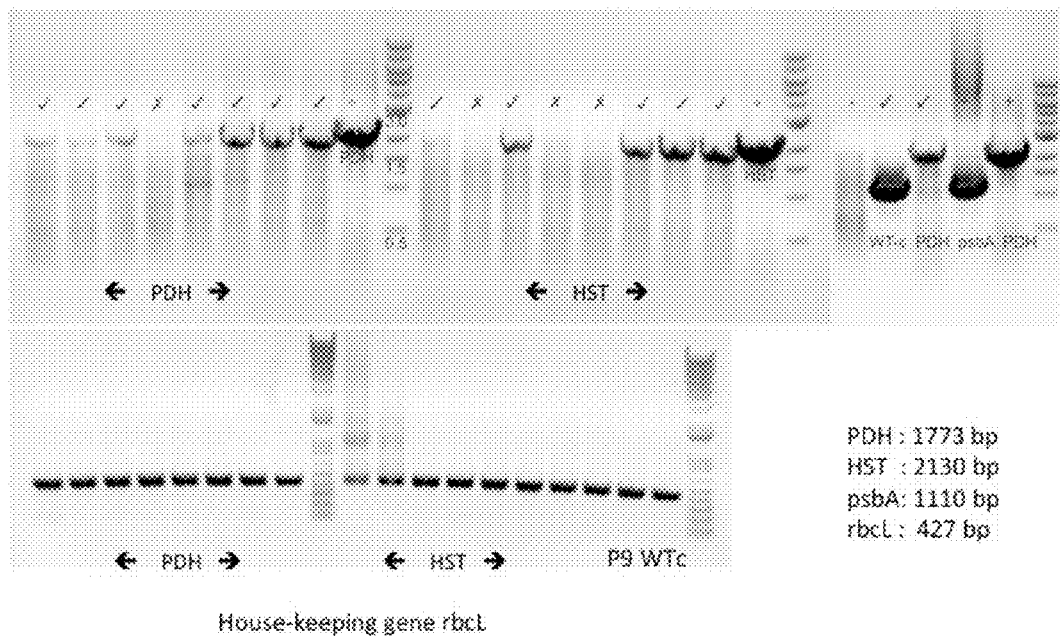
FIGS. 3A and 3B are a pair of digital images of gels showing PCR identification of positive transgenic PDH or HST lines after transformation and selection on HS media (FIG. 3A) or RT-PCR confirmation of selected PDH transgenic cell lines (FIG. 3B). Check marks indicate positive transgenic lines; "X" marks indicate negative cell lines, "+" indicates plasmid positive control, and "−" indicates negative control.

Positive colonies (able to grow photosynthetically, on high salt (HS) media) were picked and moved to fresh HS-Amp 50 plates. The freshly growing colonies were then picked and suspended in 50 μL of 5% CHELEX®-100 resin (Bio-Rad Laboratories, Hercules, Calif.) followed by heat denaturation for 10 minutes at 98° C. Then 2 μL of the extract was used as a template for the PCR reaction, using the KOD polymerase kit. The reaction mix for a single reaction was 25 μL 2× buffer, 10 μL dNTP mix, 1.5 μL each of forward and reverse primers, 2.0 μL template, 1.0 μL KOD polymerase, and 9.0 μL water. The same set of primers was used for PDH and HST, since they were expressed under the control of the same promoter and terminator (Forward primer: 5'-CTAGGCAGTGGCGCGATGAC-3' (SEQ ID NO: 5); Reverse primer: 5'-GGCCGCTCTAGCTA-GAACTAGTGG-3' (SEQ ID NO: 6)). The psbA gene was also amplified as a control (Forward primer: 5'-ATGACA-GCAATTTTAGAACGTCG-3' (SEQ ID NO: 7), Reverse primer: 5'-TAGAACGTCGTGAAAATTCTAGCCTATGG-3' (SEQ ID NO: 8)). PCR conditions were 2 minutes at 94° C., 35 cycles of 10 seconds at 98° C., 30 seconds at 56° C. and 2.5 minutes at 68° C., followed by 6 minutes at 68° C. PCR products were detected by ethidium bromide staining on 0.8-1% agarose gels. Multiple lines positive for PDH or HST were identified (FIG. 3A).

Expression of PDH was tested with RT-PCR. RNA was extracted from 5 mL of cell culture pelleted by centrifuging for 5 minutes at room temperature. The pellet was frozen in liquid nitrogen and processed for RNA isolation or stored at −80° C. for later use. TRIZOL® reagent (1 mL, Invitrogen/Life Technologies, Carlsbad, Calif.) was added to the cell pellet, vortexed until homogenous and incubated at room temperature for 5 minutes. Then 200 μL of chloroform was added, vortexed for 15 seconds, and incubated at room temperature for 3 minutes. The sample was centrifuged for 15 minutes at 4° C. to eliminate debris and the aqueous phase was transferred to a fresh tube. The sample was then mixed with 500 μL of isopropanol and incubated at room temperature for 10 minutes. The RNA was pelleted by centrifugation at 4° C. for 10 minutes, washed once with 1 mL 80% ethanol, and repelleted by centrifuging for 5 minutes at 4° C. The RNA was air dried and resuspended in 100 μL water at 55° C. for 10-15 minutes.

Figure 3B:
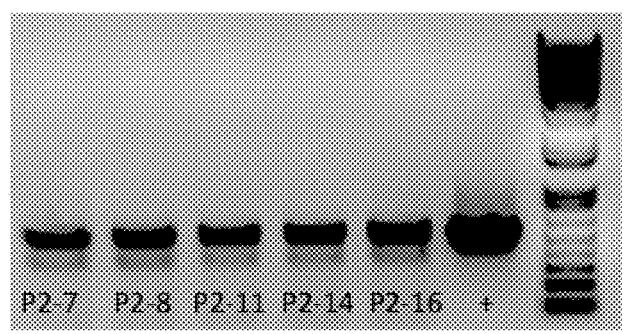

The isolated RNA was treated with DNase for 1 hour at 37° C. followed by inactivation of the DNase. cDNA was synthesized with 10 μL of the RNA mix using gScript™ cDNA Super Mix (Quanta Biosciences, Gaithersburg, Md.). RT-PCR of PDH was carried out with forward primer 5'-CCGCTGAAAAAAGAAATACATAA-3' (SEQ ID NO: 9) and reverse primer 5'-CTTTTTTCAGCGGC-CGAACGG-3' (SEQ ID NO: 10). The reaction mix was 2 μL Taq buffer, 1 μL dNTP mix, 0.5 μL each primer, 2.0 μL template, 0.5 μL Blue Taq polymerase, and 13.5 μL water. PCR conditions were 3 minutes at 94° C., 30 cycles of 30 seconds at 94° C., 30 seconds at 58° C., and 2.5 minutes at 72° C., followed by 5 minutes at 72° C. Samples (20 μL) were loaded on 0.8-1% agarose gels and products detected by ethidium bromide staining. The expected PDH amplification fragment was about 450 bp. Expression of PDH in five independent cell lines was confirmed by RT-PCR (FIG. 3B).

EXAMPLE 2

Characterization of PDH and HST Transgenic Algae

This Example describes characterization of non-photochemical quenching (NPQ), quinone reoxidation kinetics, and cell growth of transgenic algae expressing heterologous PDH or HST proteins.

Non-photochemical quenching (NPQ) was measured in wild type (WT) algae, four HST transgenic lines, and three PDH transgenic lines. For quinone reoxidation kinetics and fluorescence induction studies, cell suspensions of the complemented WT and transgenic *Chlamydomonas* cells were adjusted to a chlorophyll (Chl) concentration of about 5 μg Chl/mL. The protocol to measure the quinone reoxidation kinetics, measures $F_0$, before executing a single-turnover flash, and the fluorescence decay was monitored for 100 seconds. For fluorescence induction, the protocol measured $F_0$ followed by slow induction (~750 μmoles at 650 nm). The cells were dark adapted for 10 minutes prior to the experiment. The quinone reoxidation kinetics were fit using the Origin software according to Vass et al. (*Biochemistry* 38: 12786-12794, 1999).

Figure 4:
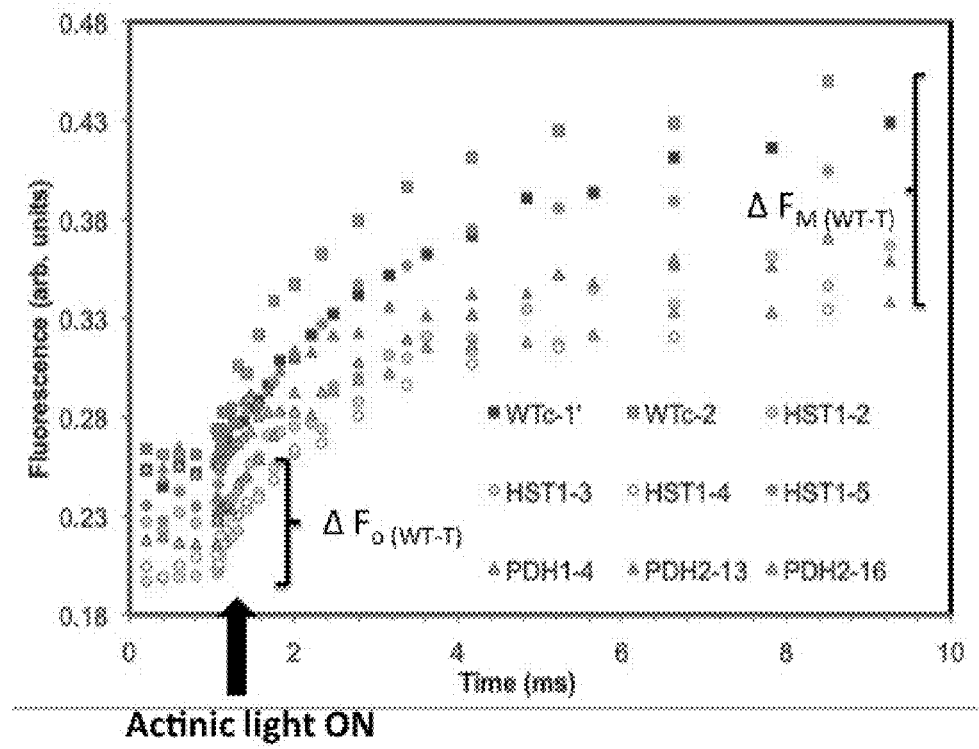
FIG. 4 is a graph showing chlorophyll fluorescence kinetics of WT-complement (WT-c), HST transgenic, and PDH transgenic algae lines before and after an actinic flash.
Figure 5A:
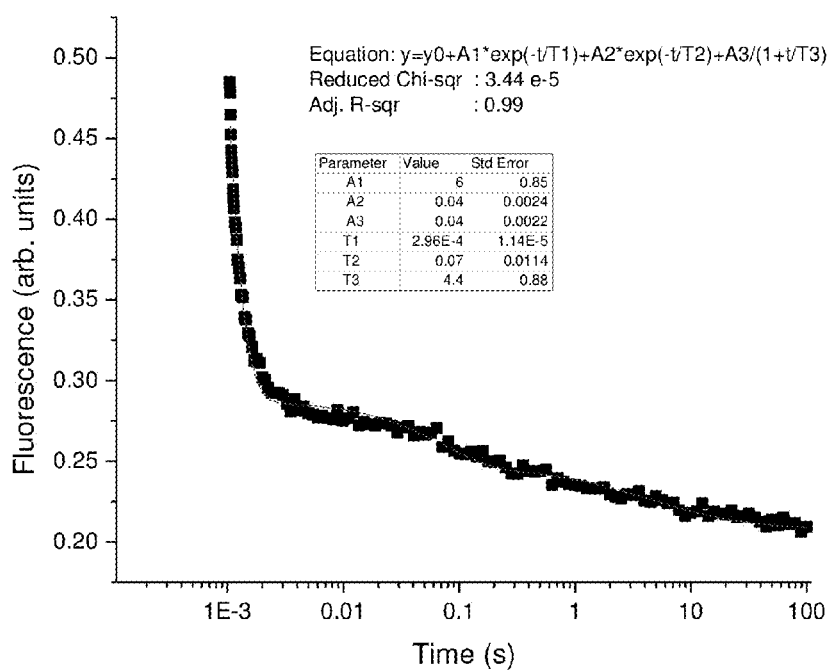
FIGS. 5A-5C are a series of graphs showing quinone reoxidation kinetics of WT-c (FIG. 5A), PDH1-4 line (FIG. 5B), and PDH2-16 line (FIG. 5C). The curves were fit using three independent exponential rate constants using the equations shown. A=amplitude of rate constant. T=rate constant in seconds.
Figure 5B:
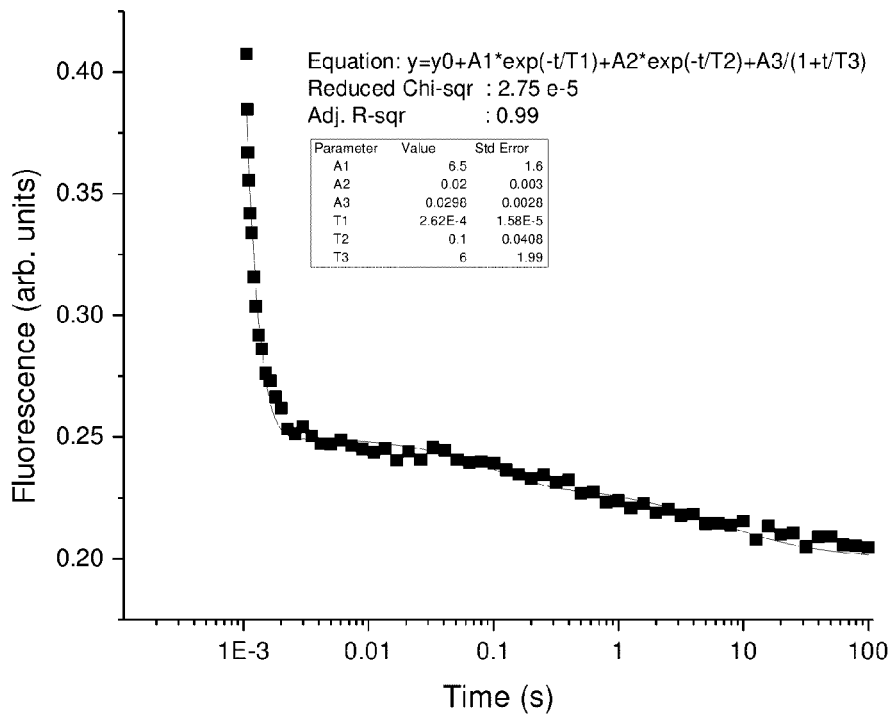
Figure 5C:
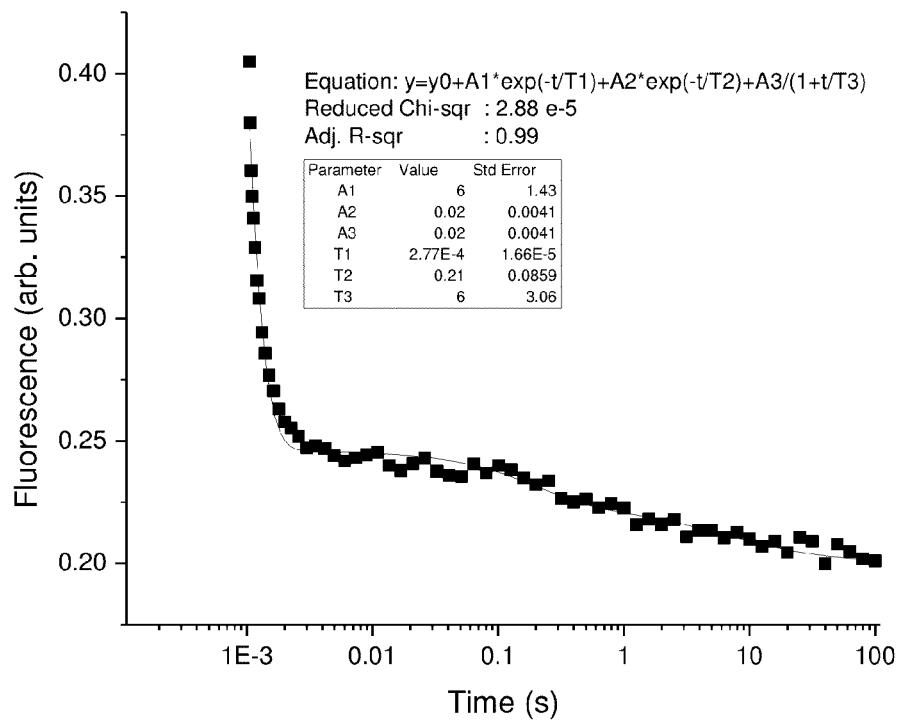

As shown in FIG. 4, the transgenic algae had reduced minimal fluorescence ($F_0$) and maximal fluorescence ($F_m$) as compared to the WT complement algae. This indicates that NPQ was reduced in the transgenic algae and suggests the presence of an excess pool of oxidized PQ. The kinetics of quinone reoxidation were also increased (FIGS. 5A-B) in PDH cell lines, further supporting the presence of an excess pool of PQ. The life-time component (T2) was faster in the PDH cell lines compared to the WT line, while the T1 and T3 rate constants were similar between WT and transgenic cells (Table 2). The T2 component represents the oxidation of $PQH_2$ (membrane PQ pool) not bound to the Q0 site (the oxidation site at the Cytv6f complex) at the time of the actinic flash. A faster T2 component represents an overall increase in the kinetics achieved by overcoming the diffusional constraints with an increased PQ pool size.

TABLE 2

Summary of chlorophyll fluorescence decay life-time components and their amplitudes

| Cell Line | T1 (μs)/A1 (%) | T2 (ms)/A2 (%) | T3 (s)/A3 (%) |
|---|---|---|---|
| WT-complement | 277/99.2 | 210/0.31 | 6/0.46 |
| PDH1-4 | 262/99.2 | 100/0.33 | 6/0.33 |
| PDH2-16 | 296/99.5 | 70/0.25 | 4.4/0.25 |

To determine whether transgenic algae lines with elevated PQ levels performed as well as WT algae in fluctuating environments, the growth of the cell lines was measured in a Phenometric ePBR (Phenometric, Inc., Lansing, Mich.) programmed for a fluctuating light cycle (FIG. 6A) or a regular light-dark cycle (FIG. 6B). The lowest and highest intensities (0 and 2000 μmole photons, respectively) were the same in the fluctuating profile and the regular profile.

Figure 7:
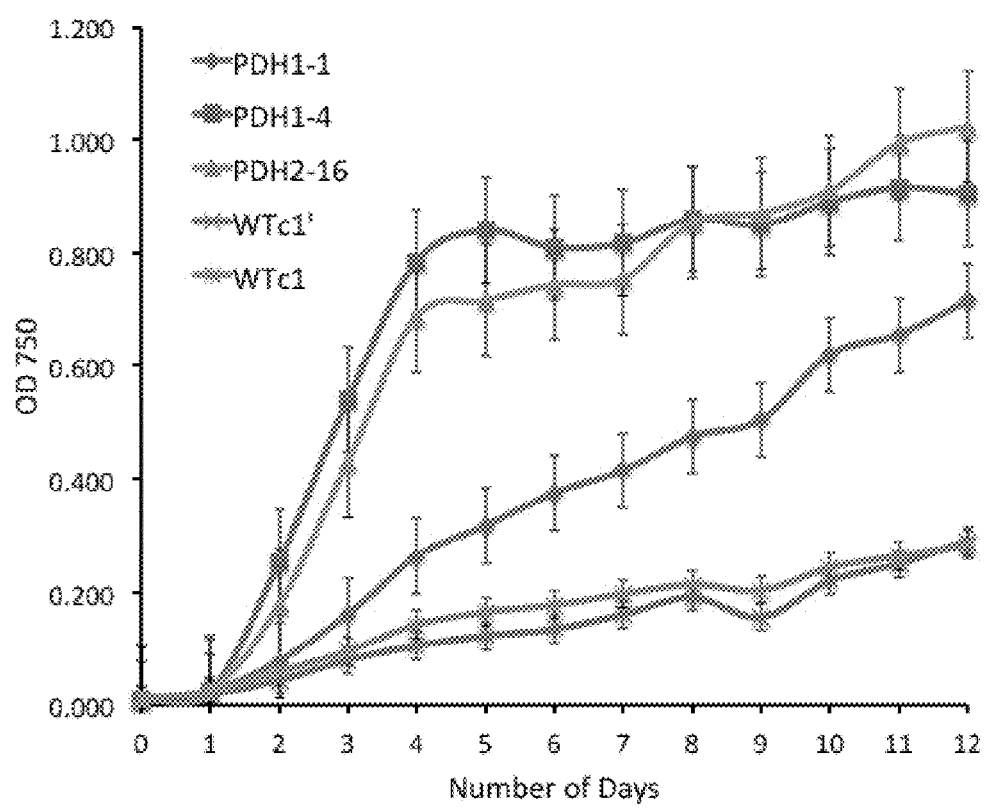
FIG. 7 is a graph showing growth of three PDH transgenic and two WT-c cell lines under fluctuating light conditions in Phenometrics (15 cm deep) photobioreactors.

The fluctuating light cycle was 13 hours (rather than 12 hours in the regular light-dark cycle) to provide similar amounts of light during the day (14,625 µmole photons for fluctuating and 15,360 µmole photons for regular). The transgenic PDH cell lines had 3-5-fold higher biomass accumulation yield than the WT cells in the fluctuating light profile over a period of 12 days (FIG. 7). Both the growth rate and the total biomass accumulation were increased in the PDH transgenic cell lines.

The results presented in this Example indicate that the PQ pool size was increased in PDH transgenic cell lines as compared to the WT cells. The transgenic cells also exhibited increased growth in fluctuating light conditions compared to the WT cells.

EXAMPLE 3

Generation of PDH/HST Transgenic Algae

This example describes the production of transgenic algae cell lines expressing heterologous PDH and HST proteins.

Figure 8:
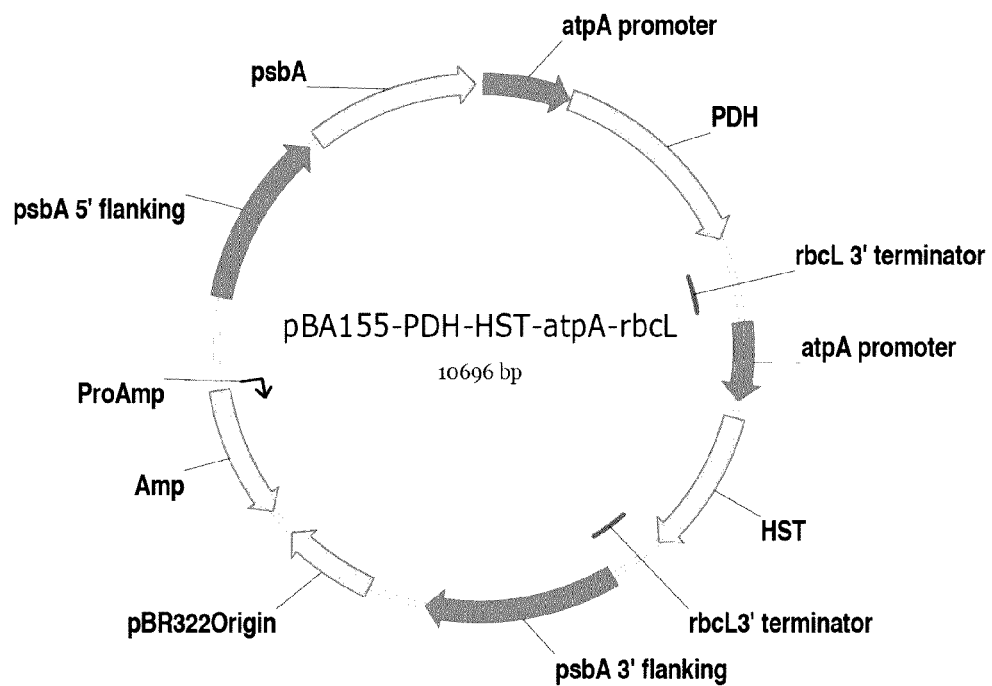
FIG. 8 is a schematic diagram of a PDH/HST expression vector used to generate transgenic *Chlamydomonas reinhardtii* cell lines.

A chloroplast transformation vector was used to express both the pdh and hst genes in algae cells. The pBA155 vector, which restores photosynthesis upon successful homologous recombination of the psbA gene (coding for the D1 protein of photosystem II), along with the gene of interest (Minagawa and Crofts, *Photosynth. Res.* 42:121-131, 1994) was utilized, as described in Example 1. Both a codon-optimized yeast PDH encoding nucleic acid (SEQ ID NO: 1) and an *A. thaliana* HST-encoding nucleic acid (SEQ ID NO: 3) were inserted in the pBA155 vector, each of which were expressed under the control of a strong promoter, atpA (FIG. 8).

Figure 9:
FIG. 9 is a digital image of a gel showing PCR identification of positive transgenic PDH/HST lines after transformation and selection on HS media. Check marks indicate positive transgenic lines; "+" indicates plasmid positive control.
Figure 9:
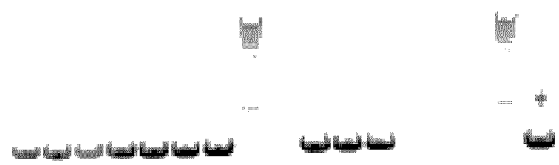

The psbA-deficient *Chlamydomonas reinhardtii* strain CC-4147 was transformed as described in Example 1. Positive colonies (able to grow photosynthetically on high salt (HS) media) were picked and moved to fresh HS-Amp 50 plates. Colonies were analyzed for presence of PDH and HST by PCR as described in Example 1. Multiple lines positive for both PDH and HST were identified (FIG. 9). Two cell lines (PH-6 and PH-14) were selected for use in subsequent experiments.

EXAMPLE 4

Characterization of PDH/HST Transgenic Algae

This Example describes characterization of chlorophyll fluorescence kinetics of transgenic algae expressing both heterologous PDH and HST proteins.

Figure 10:
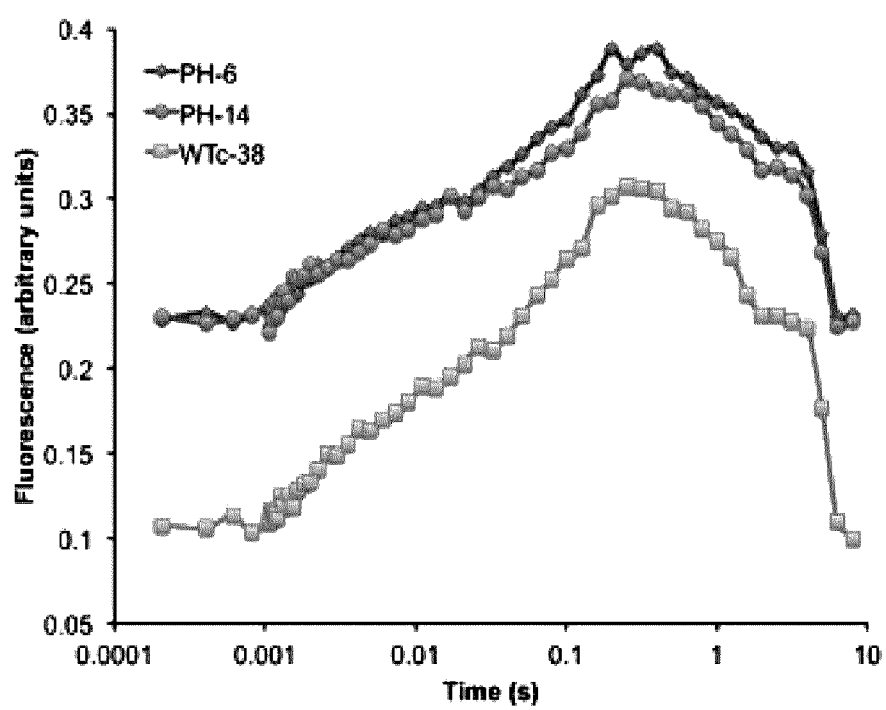
FIG. 10 is a graph (top) and table (bottom) showing raw chlorophyll fluorescence induction kinetics of two PDH/HST transgenic cell lines (PH-6 and PH-14) and a wild-type cell line (WTc-38).
Figure 11:
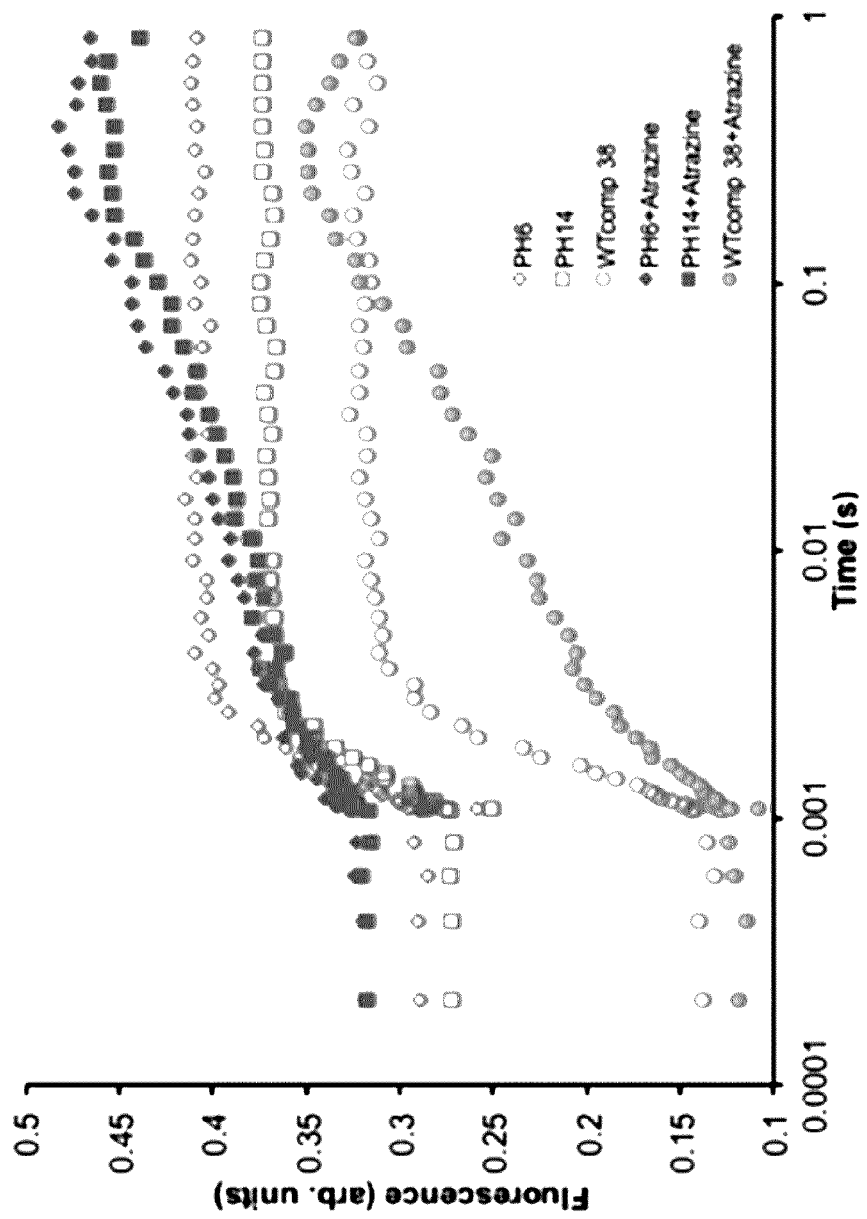
FIG. 11 is a graph showing chlorophyll fluorescence induction kinetics in two PDH/HST transgenic cell lines (PH-6 and PH-14) and a wild-type cell line (WTc-38) in the presence and absence of the photosystem II inhibitor atrazine (10 µM).

Fluorescence induction curves of algae samples normalized to 5 µg/µl Chl content were measured with and without 10 µM atrazine. Based on analysis of Chl fluorescence kinetics (FIGS. 10 and 11), a reduction in variable Chl fluorescence ($F_v=F_m-F_o$) and the $F_v/F_m$ (maximum) ratio was observed in the PDH/HST transgenic lines both in the absence and presence of atrazine (which binds to Qb site inhibiting photosystem II electron transfer) following induction with sub-saturating light relative to wild type. Without being bound by theory, these results are consistent with both an increase in PQ levels and a disconnection of the light harvesting antenna from the photosystem II reaction center, respectively. The latter observation is also consistent with an apparent reduction in light harvesting antenna size potentially increasing the quantum yield of photosynthesis (Yaakoubd et al., *Photosynthesis Research* 74:251-257, 2002; Kurreck et al., *Photosynthesis Research* 63:171-182, 2000; Perrine et al., *Algal Research* 1:134-142, 2012).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A transgenic photosynthetic cell comprising heterologous nucleic acids encoding:
   (i) a prephenate dehydrogenase (PDH) protein; and
   (ii) a homogentisate solanesyl transferase (HST) protein.

2. The transgenic cell of claim 1, wherein the heterologous nucleic acid encoding the PDH protein comprises a nucleic acid sequence having at least 90% identity to SEQ ID NO: 1.

3. The transgenic cell of claim 1, wherein the heterologous nucleic acid encoding the PDH protein encodes a PDH protein comprising an amino acid sequence at least 90% identical to SEQ ID NO: 2.

4. The transgenic cell of claim 1, wherein the heterologous nucleic acid encoding the HST protein comprises a nucleic acid sequence having at least 90% identity to SEQ ID NO: 3.

5. The transgenic cell of claim 1, wherein the heterologous nucleic acid encoding the HST protein encodes an HST protein comprising an amino acid sequence at least 90% identical to SEQ ID NO: 4.

6. The transgenic cell of claim 1, wherein the heterologous nucleic acid is expressed under the control of a constitutive promoter.

7. The transgenic cell of claim 1, wherein the heterologous nucleic acid is in an expression vector.

8. The transgenic cell of claim 7, wherein the expression vector comprises a plasmid.

9. The transgenic cell of claim 1, wherein the transgenic cell is a transgenic plant cell or a transgenic alga cell.

10. The transgenic cell of claim 9, wherein the alga cell is a *Chlamydomonas* alga cell.

11. The transgenic cell of claim 1, wherein the transgenic cell has increased amounts of plastoquinone as compared to a control cell.

12. A method of producing a photosynthetic cell comprising an increased amount of plastoquinone compared to a control cell, comprising expressing in the cell heterologous nucleic acids encoding:
   (i) a prephenate dehydrogenase (PDH) protein; and
   (ii) a homogentisate solanesyl transferase (HST) protein.

13. The method of claim 12, wherein the heterologous nucleic acid encoding the PDH protein comprises a nucleic acid at least 90% identical to SEQ ID NO: 1.

14. The method of claim 13, wherein the heterologous nucleic acid encoding the PDH protein encodes a PDH protein comprising an amino acid sequence at least 90% identical to SEQ ID NO: 2.

15. The method of claim 12, wherein the heterologous nucleic acid encoding the HST protein comprises a nucleic acid at least 90% identical to SEQ ID NO: 3.

16. The method of claim 15, wherein the heterologous nucleic acid encoding the HST protein encodes an HST protein comprising an amino acid sequence at least 90% identical to SEQ ID NO: 4.

17. The method of claim 12, wherein the cell is a plant cell or an alga cell.

18. The transgenic cell of claim 17, wherein the alga cell is a *Chlamydomonas* alga cell.

19. A method of increasing production of biomass, comprising cultivating the transgenic cell of claim 1 under conditions sufficient to produce biomass, wherein the cultivated transgenic cell produces increased biomass as compared to a control.

20. The method of claim 19, wherein the conditions sufficient to produce biomass comprise a light-dark cycle.

21. The method of claim 20, wherein the light-dark cycle comprises:
   at least one period of light of about 8-12 hours and at least one period of dark of about 12-16 hours; or
   at least one period of light of about 30 minutes to 3 hours and at least one period of dark of about 30 minutes to 3 hours.

22. The method of claim 1, wherein the culture comprising the transgenic cell is grown in a bioreactor or a raceway.

* * * * *